United States Patent [19]

Deluca et al.

[11] Patent Number: 5,571,802
[45] Date of Patent: Nov. 5, 1996

[54] METHOD OF TREATING POST MENOPAUSAL OSTEOPOROSIS WITH HEXAFLURO-VITAMIN D

[75] Inventors: Hector F. Deluca, Deerfield, Wis.; Yosuke Ogura, Tokyo, Japan

[73] Assignee: Wisconsin Alumni Research Foundation, Madison, Wis.

[21] Appl. No.: 199,991

[22] Filed: Feb. 18, 1994

Related U.S. Application Data

[63] Continuation-in-part of Ser. No. 20,218, Feb. 19, 1993.
[51] Int. Cl.$^6$ .......................... A61K 31/59; A61K 31/595
[52] U.S. Cl. .......................... 514/167; 514/168; 552/653
[58] Field of Search .................................. 514/167, 168; 552/653

[56] References Cited

U.S. PATENT DOCUMENTS

| | | | |
|---|---|---|---|
| 4,248,791 | 2/1982 | DeLuca et al. | 260/357.21 |
| 4,358,406 | 11/1982 | DeLuca et al. | 260/239.55 |
| 4,411,833 | 10/1983 | DeLuca et al. | 260/239.55 |

FOREIGN PATENT DOCUMENTS

| | | |
|---|---|---|
| 0250755 | 4/1987 | European Pat. Off. . |
| 2139627 | 11/1984 | United Kingdom . |
| WO83/00335 | 2/1983 | WIPO . |

OTHER PUBLICATIONS

"BioFactors; Vitamin D Research–First International Congress on Vitamins and Biofactors in Life Sciences", DeLuca et al, vol. 3, No. 4, pp. 271, Apr. 1992.

"Bone and Mineral; 26,27–Hexafluoro–1,25–Dihydroxyvitamin $D_3$ (F6–1,25(OH)$_2D_3$) Prevents Osteoporosis Induced by Immobilization combined with Ovariectomy in the Rat", Okumura et al, vol. 9, No. 2, pp. 101–109, May 1990.

"Bone and Mineral; Biological Potency of a Fluorinated Vitamin D Analogue in Hypoparathyroidism", Nakatsuka et al, vol. 16, No. 1, pp. 73–81, Jan. 1992.

"Archives of Biochemistry and Biophysics; 26,26,26,27,27,27–Hexafluoro–1,25–Dihydroxyvitamin $D_3$: A Highly Potent, Long–Lasting Analog of 1,25–Dihydroxyvitamin $D_3$", Tanaka et al, vol. 229, No. 1, pp. 348–354, 1984.

Tilyard, Murray W. et al., "Treatment of Postmenopausal Osteoporosis With Calcitrol or Calcium", The New England Journal of Medicine, vol. 326, No. 6, pp. 357–362 (1992).

Aloia, John F., M.D. et al, "Calcitrol in the Treatment of Postmenopausal Osteoporosis", The American Journal of Medicine, vol. 84, pp. 401–408 (1988).

*Primary Examiner*—Theodore J. Criares
*Attorney, Agent, or Firm*—Andrus, Sceales, Starke & Sawall

[57] ABSTRACT

A method of treating post menopausal osteoporosis which comprises administering to a subject having the disease an effective daily dose of 26,26,26,27,27,27-hexafluoro-1α,25-dihydroxycholecalciferol compound in an amount from about 0.05 μg to about 2.0 μg.

19 Claims, 22 Drawing Sheets

URINARY Ca/Cr, P/Cr and Mg/Cr (1 μg/man)

METHOD OF TREATING POST MENOPAUSAL OSTEOPOROSIS WITH HEXAFLURO-VITAMIN D

CROSS REFERENCE TO RELATED APPLICATION

This application is a continuation-in-part of Ser. No. 08/020,218 filed Feb. 19, 1993.

BACKGROUND OF THE INVENTION

The present invention relates to a novel method of treating diseases resulting from calcium metabolism disorders. More specifically, this invention relates to a method comprising the use of 26,26,26,27,27,27-hexafluoro-1α,25-dihydroxycholecalciferol, a derivative of vitamin $D_3$.

Vitamin $D_3$ is a well-known agent for the control calcium and phosphorous homeostasis. It is also now well known that to be effective, vitamin Da must be converted to its hydroxylated forms. For example, the vitamin is first hydroxylated in the liver to form 25-hydroxyvitamin $D_3$ and is further hydroxylated in the kidney to produce 1α,25-dihydroxyvitamin $D_3$ or 24,25-dihydroxy vitamin $D_3$. The 1α-hydroxylated form of the vitamin is generally considered to be the physiologically active or hormonal form of the vitamin and to be responsible for what are termed the vitamin D-like activities, such as increasing intestinal absorption of calcium phosphate, mobilizing bone mineral, and reabsorbing calcium in the kidneys.

Since the discovery of biologically active metabolites of vitamin $D_3$ there has been much interest in the preparation of structural analogs of these metabolites, because such compounds may represent useful therapeutic agents for the treatment of diseases resulting from calcium metabolism disorders. A variety of vitamin D-like compounds have been synthesized. See, for example, U.S. Pat. Nos. 3,741,996 directed to 1α-hydroxycholecalciferol; 3,907,843 directed to 1α-hydroxyergocalciferol; 3,786,062 directed to 22-dehydro-25-hydroxycholecalciferol; 3,906,014 directed to 3-deoxy-1α-hydroxycholecalciferol; and 4,069,321 directed to the preparation of various side chain-fluorinated vitamin $D_3$ derivatives and side chain-fluorinated dihydrotachysterol analogs.

A fluoro derivative of the accepted hormonal form of vitamin $D_3$, 1,25-dihydroxycholecalciferol (1,25-$(OH)_2D_3$), of particular interest is 24,24-difluoro-1,25-$(OH)_2D_3$ because it is characterized by at least as great if not greater activity than 1,25-$(OH)_2D_3$ (see U.S. Pat. No. 4,201,881).

Also of interest is the 26,26,26,27,27,27-hexafluoro derivative of 25-hydroxycholecalciferol (see U.S. Pat. No. 4,248,791) and the 26,26,26,27,27,27-hexafluoro derivative of 1α,25-dihydroxycholecalciferol (see U.S. Pat. No. 4,358,406). The latter is characterized by substantially greater vitamin D-like activity than the hormonal form of vitamin $D_3$, namely 1,25-dihydroxycholecalciferol, in its ability to stimulate calcium transport in the intestine, to mobilize calcium from bone and in its anti-rachitic activity according to the rat line test. In fact, data contained in U.S. Pat. 4,358,406 demonstrates that this latter hexafluoro derivative exhibits activity at least ten times greater than that of 1,25-(OH)2 $D_3$.

Several of these known vitamin D compounds exhibit highly potent activity in vivo or in vitro, and possess advantageous activity profiles and thus are in use, or have been proposed for use, in the treatment of a variety of diseases resulting from calcium metabolism disorders such as renal osteodystrophy, vitamin D-deficient rickets, and various type of osteoporosis. Vitamin D compounds have also been proposed for use in treating psoriasis, and certain malignancies.

It has generally been accepted, however, that increased toxicity also results from such increased activity. As a result, it is generally accepted that the administered dosage of highly active compounds needed to be appropriately reduced so as to avoid toxicity in a patient. Thus, the more highly active vitamin D compounds were no more effective in a patient than were the less active vitamin D compounds.

It is well known that females at the time of menopause suffer a marked loss of bone mass giving rise ultimately to osteopenia, which in turn gives rise to spontaneous crush fractures of the vertebrae and fractures of the long bones. This disease is generally known as postmenopausal osteoporosis and presents a major medical problem, both in the United States and most other countries where the lifespan of females reaches ages of at least 60 and 70 years. Generally, the disease which is often accompanied by bone pain and decreased physical activity, is diagnosed by one or two vertebral crush fractures with evidence of diminished bone mass. It is known that this disease is accompanied by diminished ability to absorb calcium, decreased levels of sex hormones, especially estrogen and androgen, and a negative calcium balance.

Similar symptoms of bone loss characterize estrogen-lack osteoporosis, senile osteoporosis and steroid-induced osteoporosis, the latter being a recognized result of long term glucocorticoid (cortico-steroid) therapy for certain disease states.

Methods for treating osteoporosis have varied considerably but to date no totally satisfactory treatment is yet known. A conventional treatment is to administer a calcium supplement to the patient. However, calcium supplementation by itself has not been successful in preventing or curing the disease. Another conventional treatment is the injection of sex hormones, especially estrogen, which has been reported to be effective in preventing the rapid loss of bone mass experienced in postmenopausal women. This technique, however, has been complicated by the fear of its possible carcinogenicity. Other treatments for which variable results have been reported, have included a combination of vitamin D in large doses, calcium and fluoride. The primary problem with this approach is that fluoride induces structurally unsound bone, called woven bone, and in addition, produces a number of side effects such as increased incidence of fractures and gastrointestinal reaction to the large mounts of fluoride administered. Another suggested method is to block bone resorption by injecting calcitonin or providing phosphonates.

In a study using calcitriol, i.e. 1α,25-dihydroxyvitamin $D_3$, Oloia et al, "Calcitriol In The Treatment Of Postmenopausal Osteoporosis," Amer. Jour. of Medicine, 1988, Vol. 84, pages 401–408, it was reported that calcitriol treatment reduced bone loss in women with postmenopausal osteoporosis by increasing calcium absorption and reducing bone resorption, but had no effect on bone formation. The average dose of calcitriol used in the Oloia et al study was 0.8µg per day. Hypercalciuria occurred in all subjects treated with calcitriol, and hypercalcemia occurred in 11 of 12 subjects. As a result, dietary calcium was lowered in each of the calcitriol treated patients. It was concluded in the Oloia et al study that further studies of efficacy and safety with lower dosages of calcitriol (up to 0.5µg per day) would be of interest.

In Tilyard et al, "Treatment of Postmenopausal Osteoporosis With Calcitriol Or Calcium," New England Journal of Medicine, 1992, Vol. 326, No. 6, pages 357–362, it was reported that women suffering from postmenopausal osteoporosis who received calcitriol, i.e. 1α,25-dihydroxyvitamin $D_3$, at dosages of 0.5μg per day for three years had a significant reduction in the rate of new vertebral fractures over women who were treated over the same period of time with supplemental calcium in the form of 1 gram of elemental calcium daily. Calcitriol treatment of the women in the Tilyard et al study was not accompanied by hypercalcemia of any severity, and thus it was concluded that calcitriol given orally in a dose of 0.25 μg twice a day to postmenopausal women with an average dietary calcium intake of 800 mg has limited potential to induce hypercalcemia. However, it was also concluded in the Tilyard et al study that serum calcium concentrations should be monitored in patients receiving calcitriol therapy due to the possibility of hypercalcemia as a side effect of such treatment.

In view of the results published by Oloia et al and Tilyard et al, calcitriol may be a viable therapeutic option in the treatment of women with postmenopausal osteoporosis. However, there is a relatively small dosage "window" or tolerance between effectiveness and toxicity resulting in the necessity to closely monitor calcitriol dosages as well as dietary calcium intake in order to avoid hypercalcemia. Thus, the potential of calcitriol to induce hypercalcemia has limited the use of calcitriol to treat postmenopausal osteoporosis as well as other diseases resulting from calcium metabolism disorders.

U.S. Pat. No. 4,255,596 suggests the use of various metabolites of vitamin $D_3$ for increasing calcium absorption and retention within the body of mammals displaying evidence of or having a physiological tendency toward loss of bone mass. The metabolites specifically named in that patent, i.e., 1α-hydroxyvitamin $D_3$, 1α,25-hydroxyvitamin $D_2$, 1α,25-dihydroxyvitamin $D_3$, 1α,25-dihydroxyvitamin $D_2$ and 1,24,25-trihydroxyvitamin $D_3$, although capable of the activity described and claimed in that patent, are also characterized by the disadvantage of causing hypercalcemia, especially if used with the conventional calcium supplement treatment. Therefore, use of these compounds to treat osteoporosis has not been widely accepted. U.S. Pat. Nos. 3,833,622 and 3,901,928 respectively suggest using the hydrate of 25-hydroxyvitamin $D_3$ and 1α-hydroxyvitamin $D_3$ for treatment of osteoporosis in a general expression of utility for those compounds. It is well known that both of those compounds express traditional vitamin D-like activity, including the danger of hypercalcemia.

U.S. Pat. No. 4,588,716 also suggests the use of 1α,25-dihydroxy-24-epi-vitamin $D_2$ to treat bone disorders characterized by the loss of bone mass, such as osteoporosis. Although this compound expresses some of the vitamin D-like characteristics affecting calcium metabolism such as increasing intestinal calcium transport and stimulating the mineralization of new bone, it has the advantage of minimal effectiveness in mobilizing calcium from bone. The 24-epi compound may be administered alone or in combination with a bone mobilization-inducing compound such as a hormone or a vitamin D compound such as 1α-hydroxyvitamin $D_3$ or $-D_2$, or 1α,25-dihydroxyvitamin $D_3$ or $-D_2$.

SUMMARY OF THE INVENTION

It has now been found that diseases resulting from calcium metabolism disorders may be effectively treated by the administration of sufficient amounts of a hexafluoro vitamin $D_3$ compound. More specifically, a method of treating diseases resulting from calcium disorders comprises the administration of an effective mount of 26,26,26,27,27,27-hexafluoro-1α,25-dihydroxyvitamin $D_3$. The above compound may be administered alone or in combination with other pharmaceutically acceptable agents. Dosages of from not less than about 0.05 μg/day to not more than about 2.0 μg/day of the individual compound per se, or in combinations, are generally effective. This method has the distinct advantage that it will treat the disease, and at the same time this compound advantageously will not cause hypercalcemia even if the compound is administered continuously on a daily basis, as long as the appropriate compound dosages are used, it being understood that the dosage levels will be adjusted dependent on the response of the subject as monitored by methods known to those skilled in the art. It has been discovered that the "window" or tolerance between effectiveness and toxicity of the hexafluoro compound in humans is relatively large. This results in a relatively effective and safe treatment even though the hexafluoro compound is known to be about ten times more active than a compound such as 1α,25-dihydroxyvitamin $D_3$.

The above method, involving the administration of the indicated dosages of 26,26,26,27,27,27-hexafluoro-1α,25-dihydroxyvitamin $D_3$ provides a novel method for the treatment or prevention of a variety of human diseases resulting from calcium metabolism disorders such as renal osteodystrophy, hypoparathyroidism, pseudohypoparathyroidism, hypocalcemia, osteomalacia, vitamin D-deficient rickets and various forms of osteoporosis such as postmenopausal osteoporosis, estrogen-lack osteoporosis, senile osteoporosis and steroid-induced osteoporosis. It will be evident that the method will find ready application for the prevention or treatment of disease states other than those named, in which the loss of bone mass is an indication.

DISCLOSURE OF THE INVENTION

Figure 1:
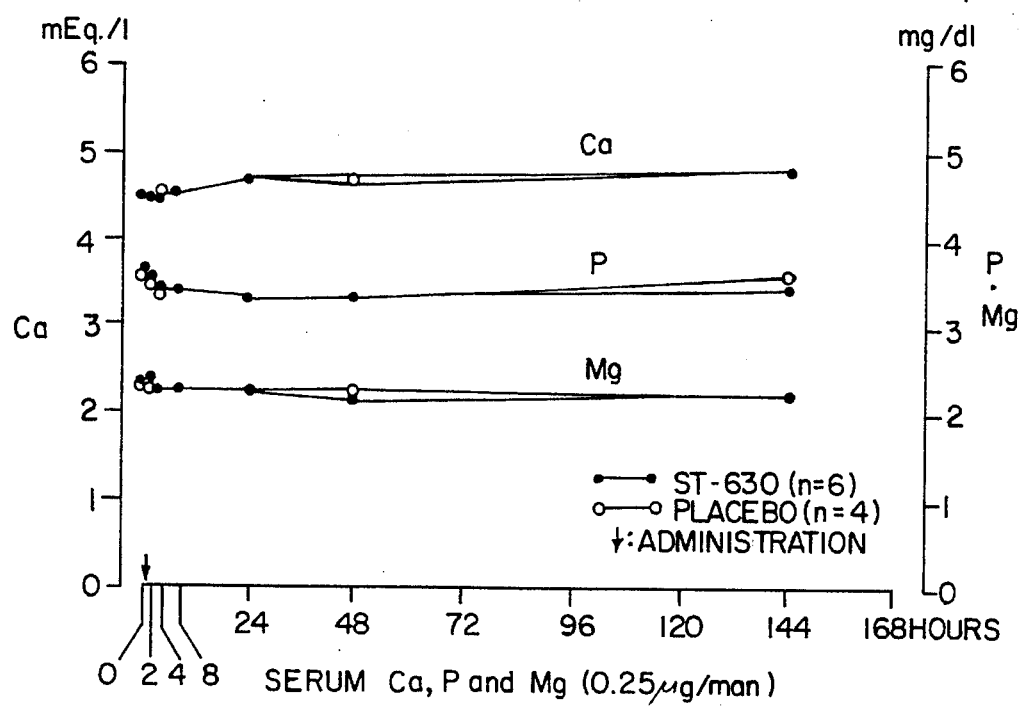
FIGS. 1–4 are graphs of blood serum concentration of Ca, P and Mg over time after administration of 0.25 μg, 0.5 μg, 1 μg and 2 μg/man of ST-630, respectively.
Figure 2:
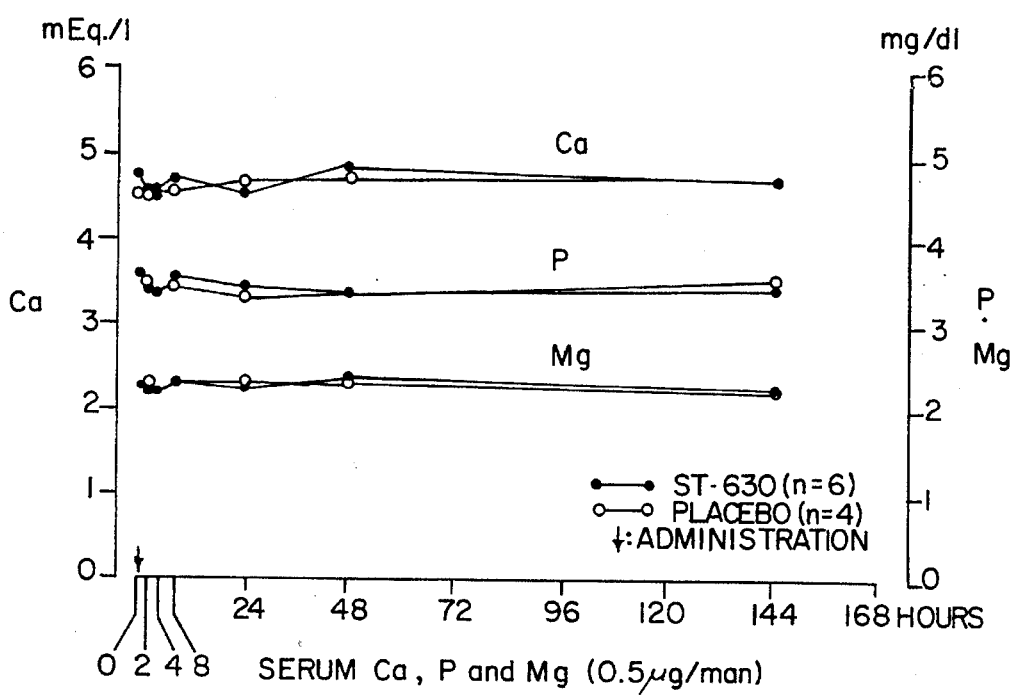
Figure 3:
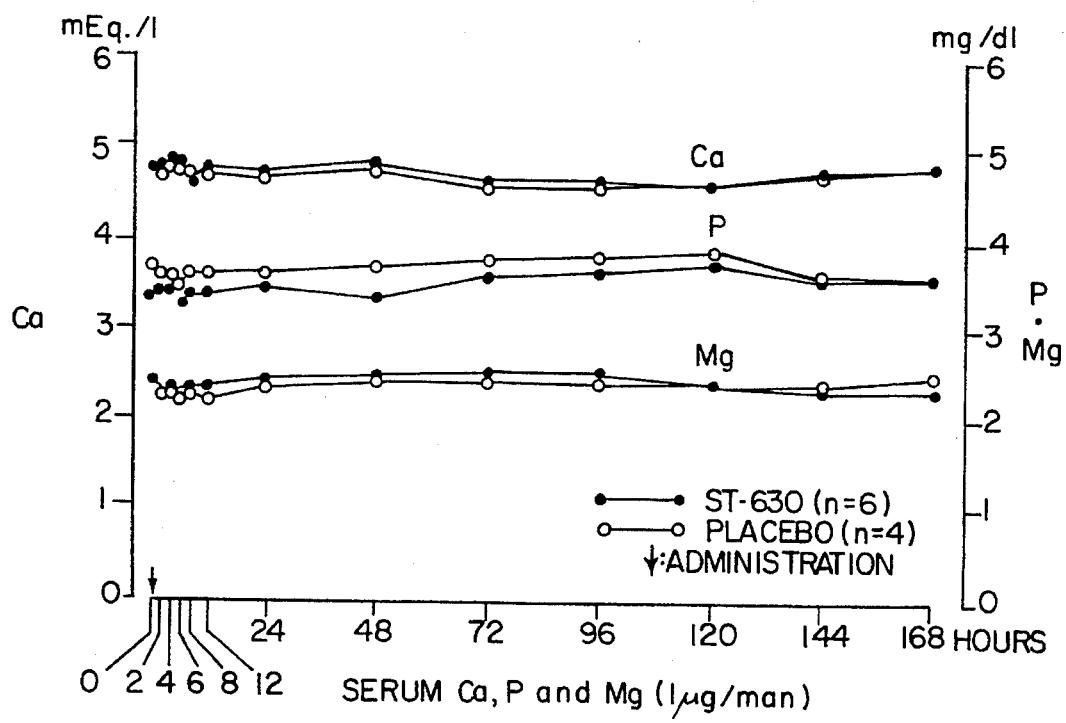
Figure 4:
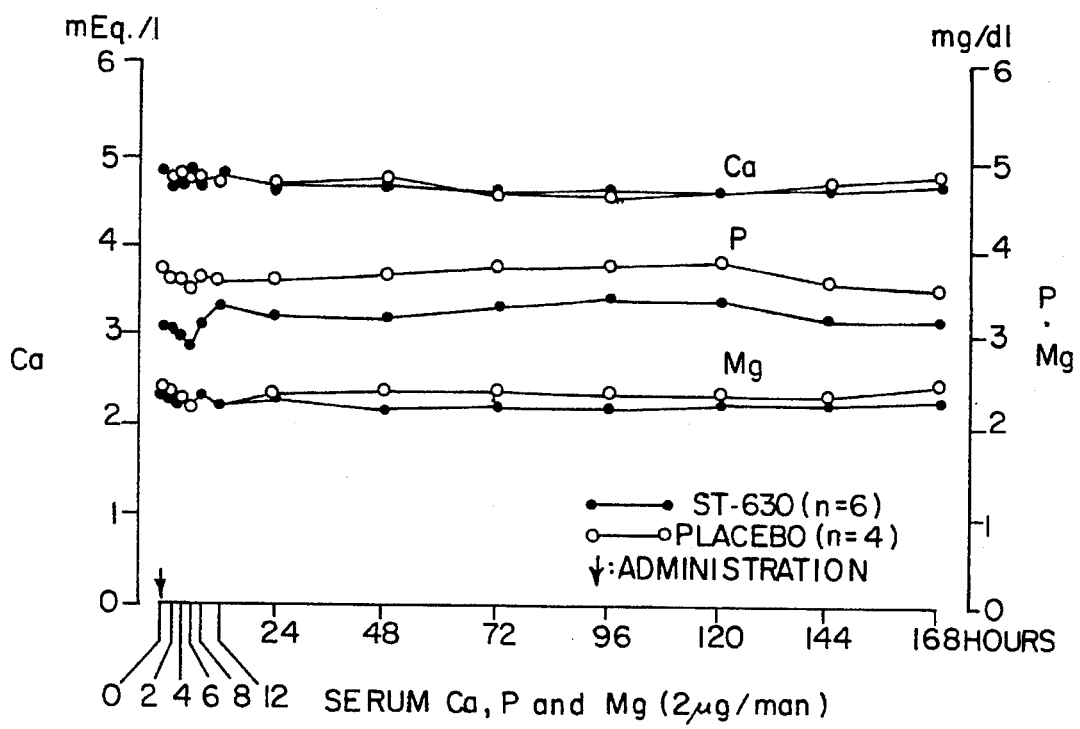
Figure 5:
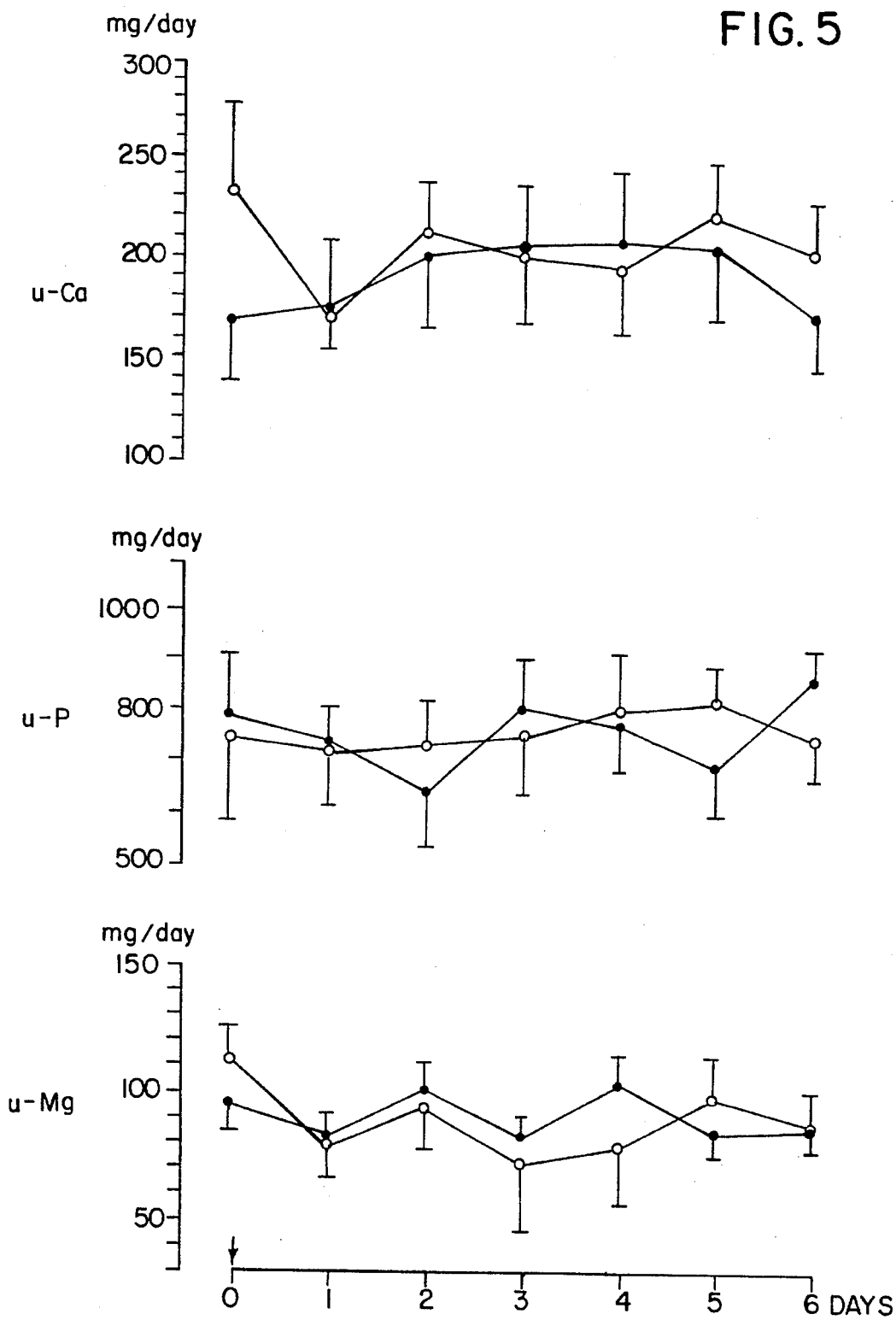
FIGS. 5–8 are graphs of urinary excretions of Ca, P and Mg over time after administration of 0.25 μg, 0.5 μg, 1 μg and 2 μg/man of ST-630, respectively.
Figure 6:
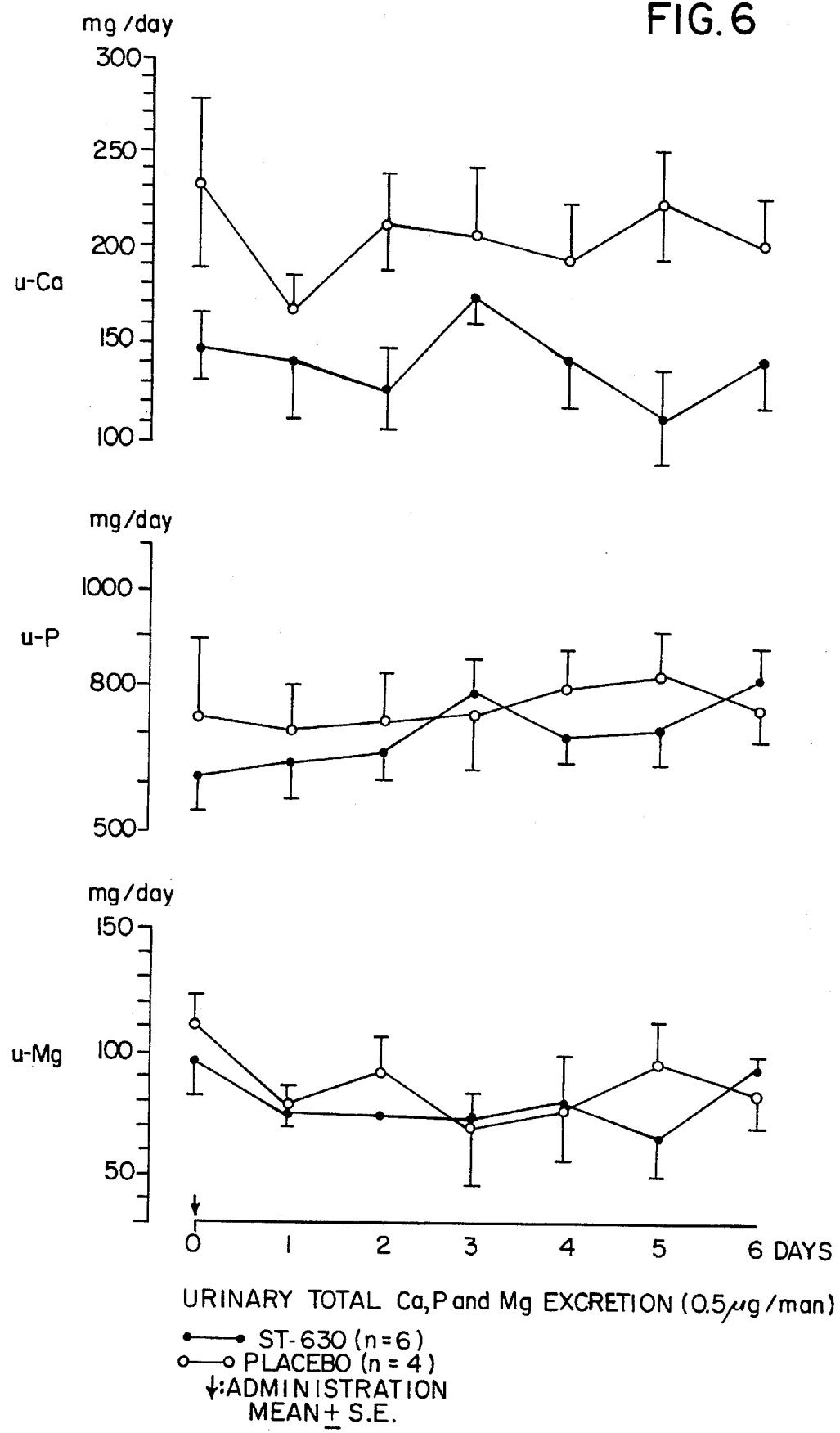
Figure 7:
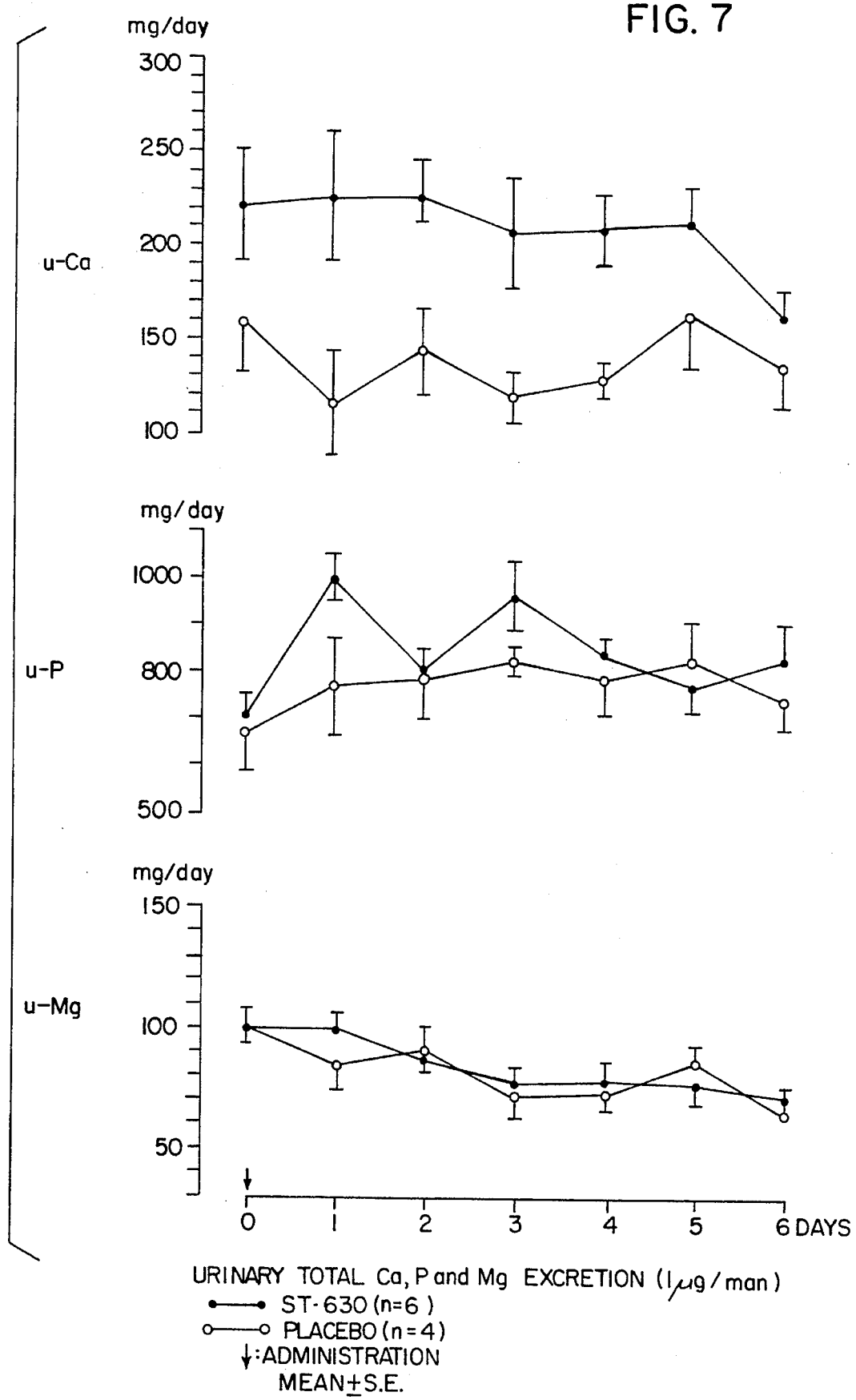
Figure 8:
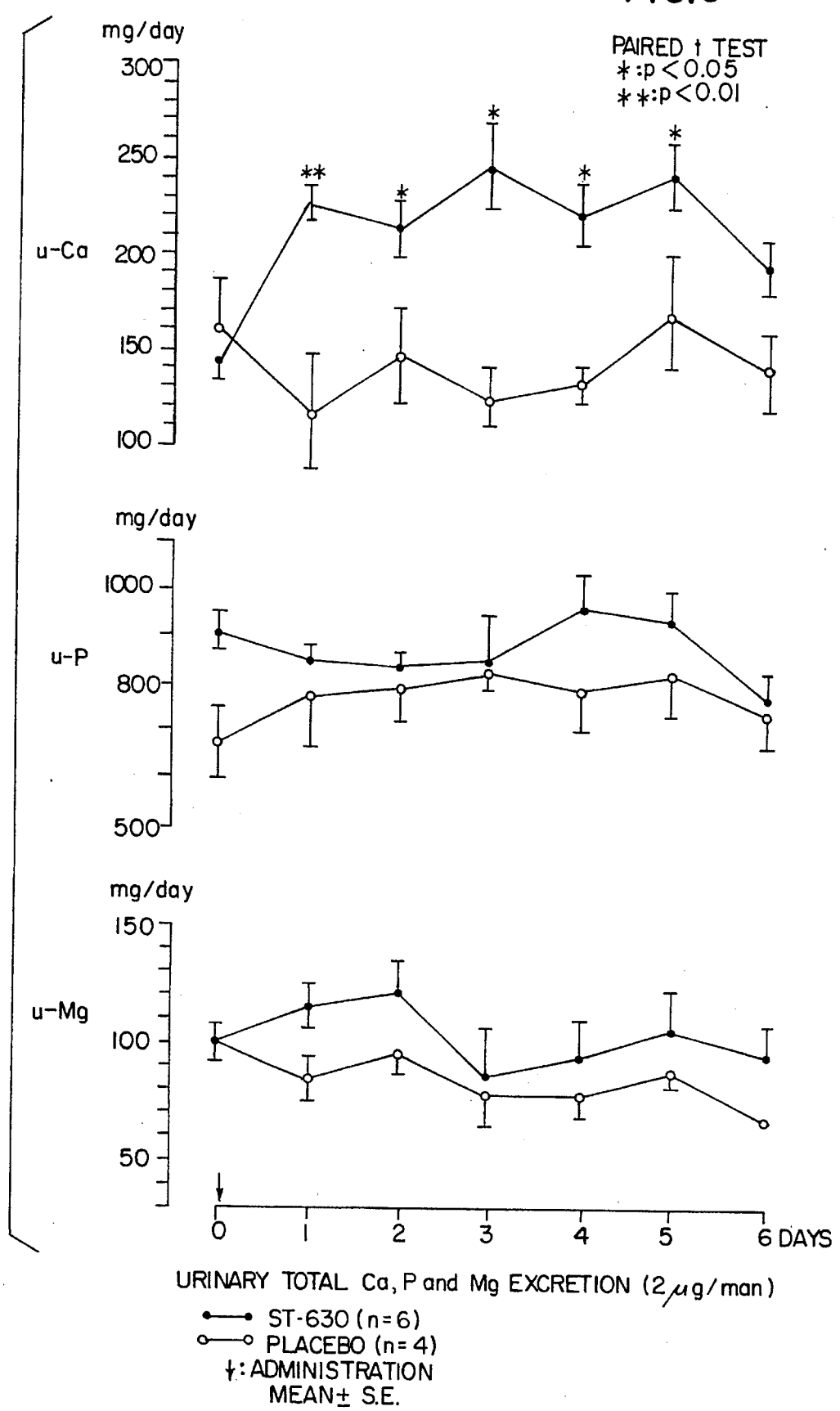
Figure 9:
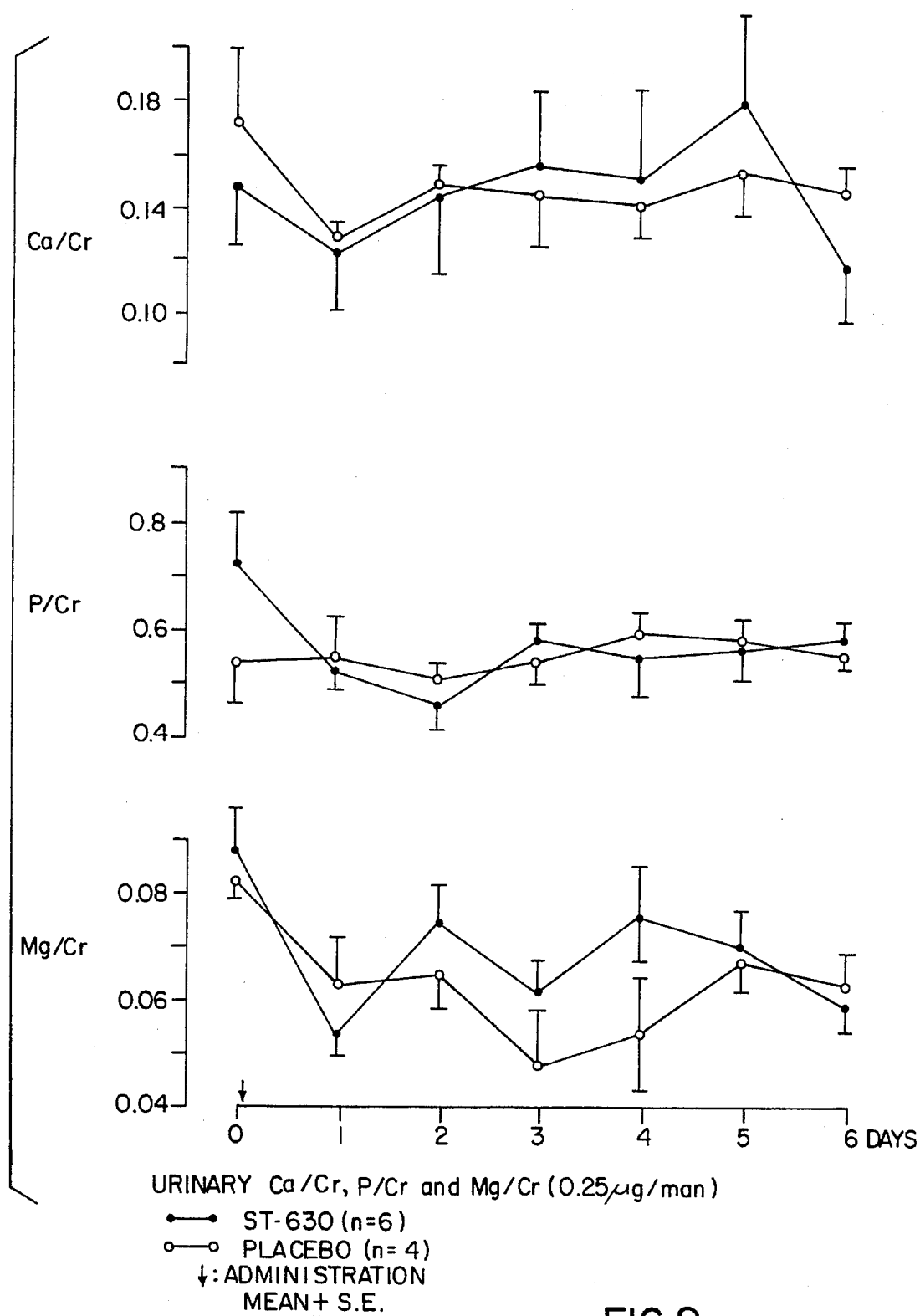
FIGS. 9–12 are graphs of urinary excretions of Ca/Cr, P/Cr and Mg/Cr ratios over time after administration of 0.25 μg, 0.5 μg, 1 μg and 2 μg/man of ST-630, respectively.
Figure 10:
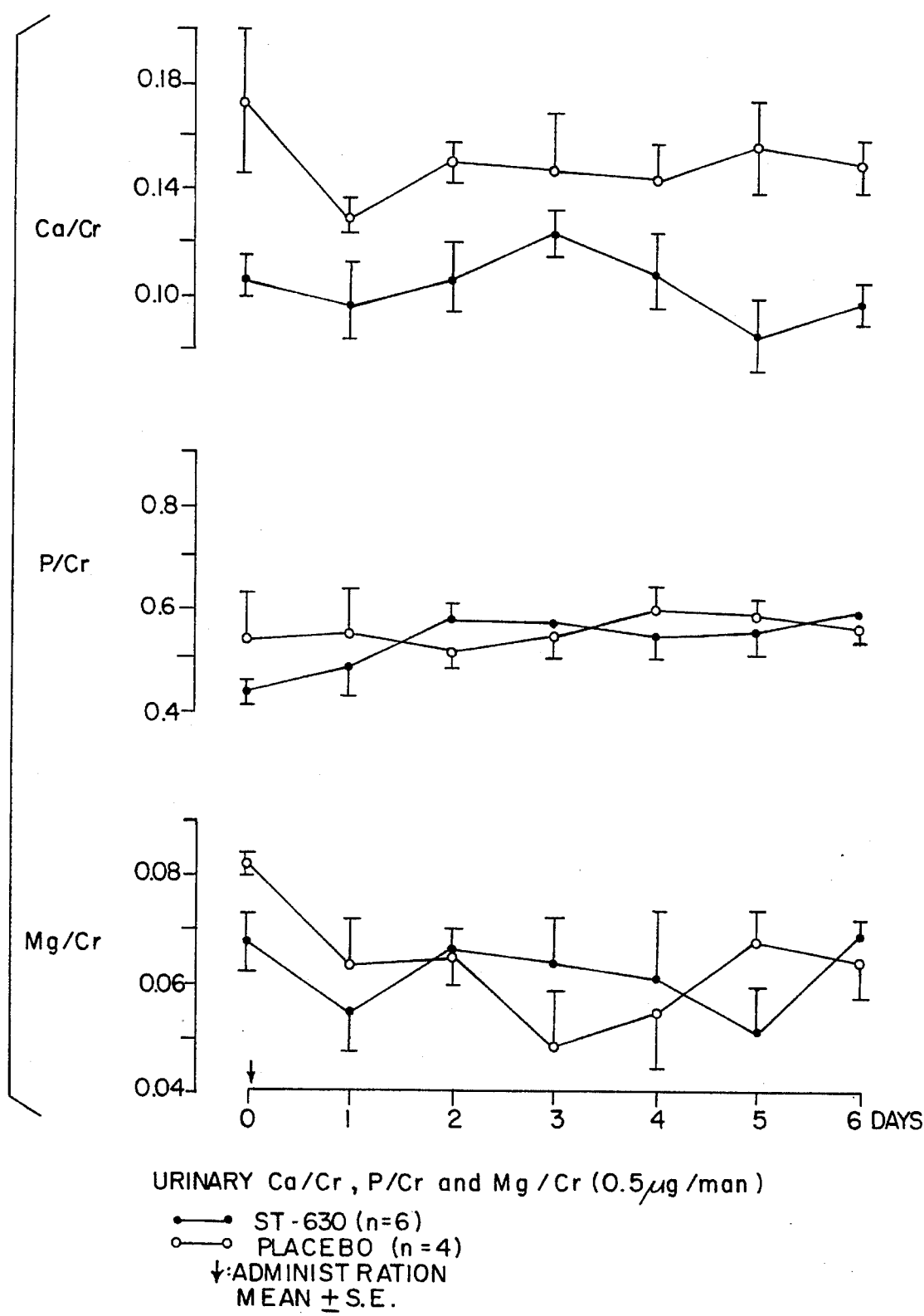
Figure 11:
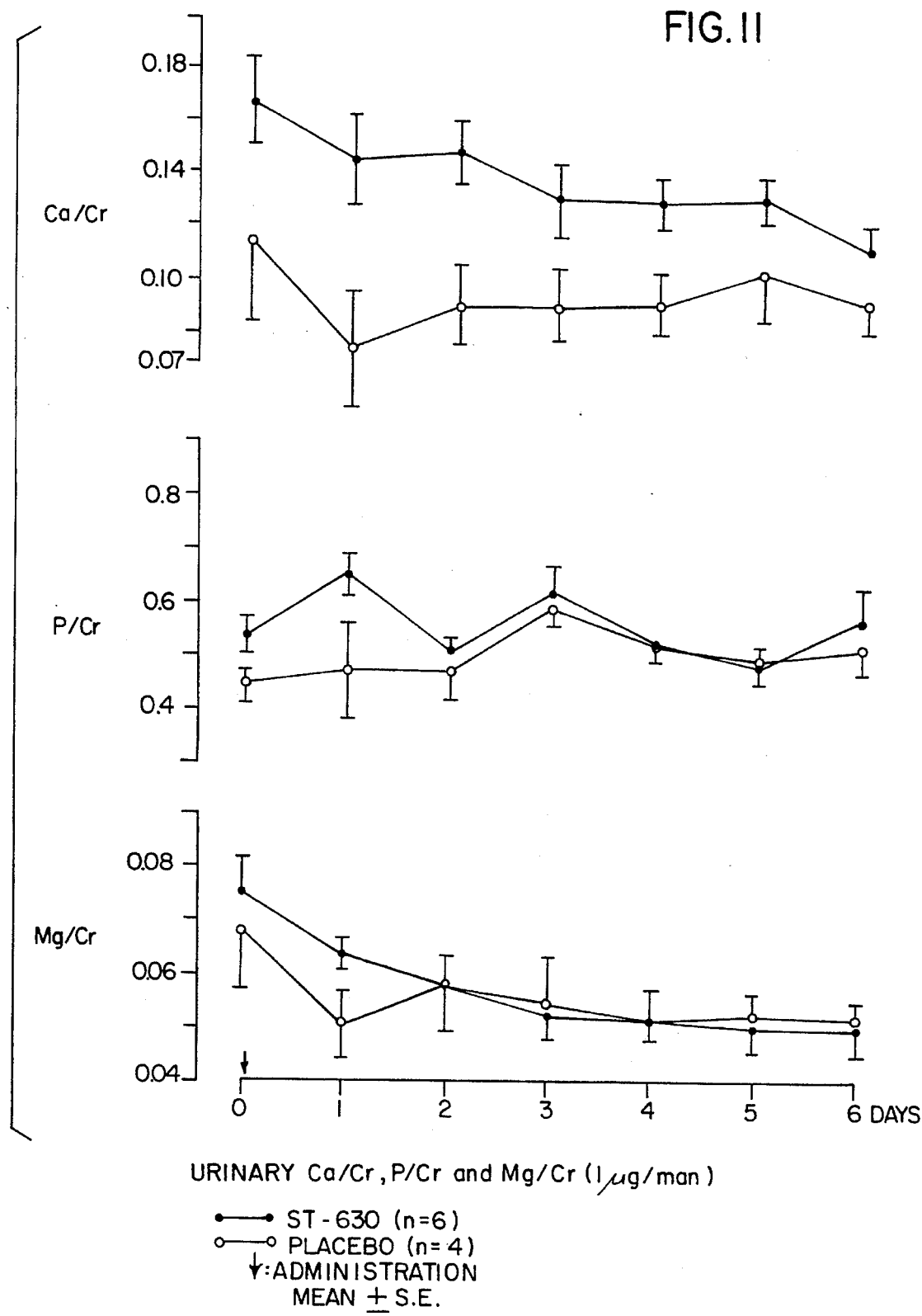
Figure 12:
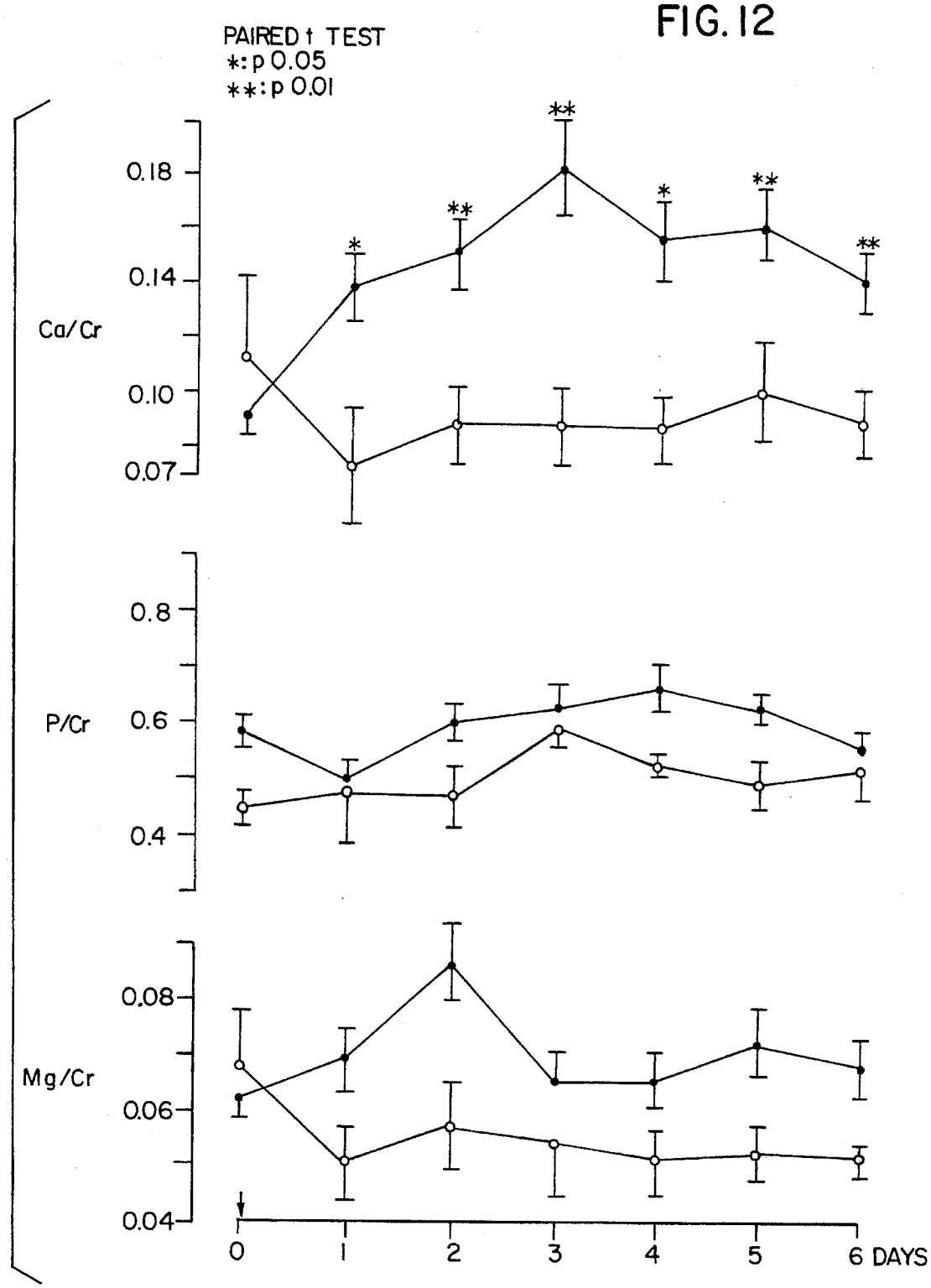

A new method for treating a variety of human diseases resulting from calcium metabolism disorders has now been discovered. The method involves the use of 26,26,26, 27,27, 27-hexafluoro- 1α,25-dihydroxycholecalciferol (26,26,26, 27,27,27-$F_6$-1α,25-$(OH)_2D_3$). It has been discovered that this highly active hexafluoro compound may be administered to a patient at dosage levels equal to those used for less active vitamin D compounds without resulting in toxicity of the patient. Thus, the "window" or tolerance between effectiveness and toxicity of the hexafluoro compound in humans has been discovered to be relatively large.

This method of treating human diseases resulting from calcium metabolism disorders comprises administering to a subject having the disease an effective daily dose of 26,26, 26,27,27,27-$F_6$-1α,25$(OH)_2D_3$ in an mount from about 0.05 μg to about 2.0 μg per day for an extended period, i.e. a minimum of at least 7 days. The preferred dosage range is dependent upon the disease being treated and the response of the patient to treatment, as is well known by those skilled in the art. For example, preferred ranges for the treatment of osteoporosis might be 0.1 μg/day to 0.5 μg/day while for the treatment of renal osteodystrophy it might be 0.1 μg/day to 0.3 μg/day.

The 26,26,26,27,27,27-$F_6$-1α,25-$(OH)_2D_3$ compound used in the method of this invention may be readily synthesized in accordance with known procedures. Reference is made to U.S. Pat. No. 4,358,406 entitled "26,26,26,27,27, 27-Hexafluoro-1α,25-Dihydroxycholecalciferol and Process for Preparing Same" issued Nov. 9, 1982 to DeLuca et al for a disclosure at Columns 2–6 therein of the synthesis of 26,26,26,27,27,27-$F_6$-1α,25-$(OH)_2D_3$, that disclosure being specifically incorporated herein by reference thereto.

The biological activity and potency of 26,26,26,27,27,27-$F_6$-1α,25-$(OH)_2D_3$ is also well known. Reference is once again made to U.S. Pat. No. 4,358,406 for a disclosure at Columns 6–8 therein of the biological activity of 26,26,26, 27,27,27-$F_6$-1α,25-$(OH)_2D_3$, that disclosure being specifically incorporated herein by reference thereto. It can be concluded from the data disclosed in U.S. Pat. No. 4,358, 406 and incorporated by reference herein that in the vitamin D responsive systems of vitamin D-deficient animals 26,26, 26,27,27,27-$F_6$-1,25-$(OH)_2D_3$ exhibits activity at least ten times greater than that of 1,25-$(OH)_2D_3$ which is the hormonal form of the vitamin and heretofore considered the most biologically potent vitamin D derivative.

Clinical studies involving the use of 26,26,26,27,27,27-$F_6$-1α,25-$(OH)_2D_3$ (hereinafter referred to as "ST-630") involved the following procedures:

1. Study design 1.1 Examination and measurement parameters
   1) Subjective symptoms
   2) Questioning, auscultation, percussion
   3) Vital Signs
      Blood pressure, heart rate, body temperature and respiratory rate
   4) ECG
   5) Laboratory tests
      (1) Hematology
         RBC, WBC, hemoglobin, platelet count. hematocrit, differential WBC, reticulocyte count and ESR
      (2) Blood biochemistry:
         Total protein fraction, BUN, creatinine, total cholesterol, neutral fat, phospholipid, serum electrolytes (Na, K, Cl, Ca, P, Mg), Al-P, GOT, GPT, LDH, γ-GTP, CPK, blood glucose, HBs antigen/antibody[*1], serologic test for syphilis, activated partial thrombo-plastin time [*2] and prothrombin time [*2]

[*1]: Performed only prior to examination,
[*2]: Performed only in the repeated-dose study, (3) Urinalysis:
         pH, occult blood, protein, glucose, bilirubin, urobilinogen, sediment and creatinine clearance (24-hour method)
   6) Clinical pharmacology
      (1) Serum concentrations:
         ST-630, Ca, P, Mg and Al-P
      (2) Urinary excretion
         ST-630, Ca, P, Mg, Na, K, creatinine, c-AMP[*3] and hydroxyproline[*3]

[*3]: Performed in the study of dietary effect and the repeated-dose study,

| Study | STEP | No. of subjects | Age | Body weight (kg) | Body height (cm) |
|---|---|---|---|---|---|
| 1.2. Background factors of the subjects | | | | | |
| Single-dose administration | 1 | 4 | 21–23 (22.0)* | 63–68 (66.6) | 166–176 (172.4) |
|  | 2 | 4 | 20–22 (20.8) | 61–83 (71.8) | 172–182 (177.8) |
|  | 3 | 4 | 20–25 (21.5) | 53–63 (58.8) | 170–178 (173.5) |
|  | 4 | 6 | 22–25 (22.7) | 53–72 (59.5) | 168–177 (173.3) |
|  | 5 | 8 | 20–23 (22.1) | 58–72 (63.3) | 168–178 (172.6) |
|  | 6 | 8 | 20–23 (21.5) | 50–74 (61.9) | 162–180 (172.6) |
|  | 7 | 8 | 20–22 (20.9) | 56–70 (64.9) | 170–180 (175.6) |
|  | 8 | 8 | 20–23 (21.0) | 50–73 (60.9) | 163–181 (172.1) |
| Dietary effect |  | 10 | 20–25 (22.3) | 54–78 (63.8) | 164–178 (172.8) |
| Repeated-dose administration |  | 8 | 20–22 (21.3) | 52–70 (59.9) | 161–178 (169.8) |

*: (): mean

2. Single-dose study

2.1. Dosage schedule

| | | No. of subjects | | | | No. of subjects | |
| --- | --- | --- | --- | --- | --- | --- | --- |
| STEP | Dose (μg) | Active drug | Placebo | STEP | Dose (μg) | Active drug | Placebo |
| 1 | 0.0125 | 2 | 2 | 5 | 0.25 | 6 | 2 |
| 2 | 0.025 | 2 | 2 | 6 | 0.5 | 6 | 2 |
| 3 | 0.05 | 2 | 2 | 7 | 1.0 | 6 | 2 |
| 4 | 0.1 | 4 | 2 | 8 | 2.0 | 6 | 2 |

| Course | | The day before treatment | Administration date | Day 2 | Day 3 | Day 4 | Day 5 | Day 6 | Day 7 | Day 15 |
| --- | --- | --- | --- | --- | --- | --- | --- | --- | --- | --- |

2.2. Study schedule

(1) Steps 1, 2, 3 and 4

| | | | | | | | | | | | | | | | |
| --- | --- | --- | --- | --- | --- | --- | --- | --- | --- | --- | --- | --- | --- | --- | --- |
| Time after administration (hr) | | −24 −18 | Administration | 0 | 2 | 4 | 6 | 8 | 12 | 24 | 48 | 72 | 96 | 120 | 144 |
| Subjective symptoms | | | | |<----------------------------------------------------------->| | | | | | | | | | |
| Questioning, auscultation percussion | | ○ | | ○ | | ○ | | ○ | | ○ | ○ | | | | ○ | ○ |
| Vital signs | | ○ | | ○ | ○ | ○ | ○ | ○ | ○ | ○ | ○ | | | | ○ | ○ |
| ECG | | ○ | | | | | | ○ | ○ | | | | ○ | ○ | | |
| Laboratory tests | | ○ | | | | | | | | | ○ | | | | ○ | ○ |
| Serum concentration | ST-630 Ca, P, Mg, Al—P | ○ | | ○* | ○* | ○ | | ○ | ○ | ○ | ○ | | | | ○ | ○ |
| Urinary excretion | ST-630 Ca, P, Mg, Cr | |<--*--------*--------*--------*-->| | | | | | | | | | | | |
| Hospitalization | | |<------------------------------------------->| | | | | | | | | | | | |
| Total amount of blood collected 105 ml 115 ml* | (Prior examination) 19 ml | | 19 ml | | 5 ml | 5 ml | | | 5 ml | 5 ml | 19 ml | | | | 19 ml | (Follow-up examination) 19 ml |

2) Steps 5 and 6

| | | | | | | | | | | | | | | | |
| --- | --- | --- | --- | --- | --- | --- | --- | --- | --- | --- | --- | --- | --- | --- | --- |
| Time after administration (hr) | | −24 −18 | Administration | 0 | 2 | 4 | 6 | 8 | 12 | 24 | 48 | 72 | 96 | 120 | 144 |
| Subjective symptoms | | | | |<----------------------------------------------------------->| | | | | | | | | | |
| Questioning, auscultation percussion | | ○ | | ○ | ○ | ○ | ○ | | ○ | ○ | | | | ○ | ○ | |
| Vital signs | | ○ | | ○ | ○ | ○ | ○ | ○ | ○ | ○ | | | | ○ | ○ | |
| ECG | | ○ | | | | | | | | ○ | ○ | | | ○ | ○ | |
| Laboratory tests | | ○ | | | | | | | | | ○ | | | ○ | ○ | |
| Serum concentration | ST-630 Ca, P, Mg, Al—P | ○ ○ | | ○ ○ | ○ ○ | | ○ ○ | | | ○ ○ | | | | ○ ○ | | |
| Urinary | ST-630 | ○ | |<------------------------*--*--*--*-->| | | | | | | | | | | |
| excretion | Ca, P, Mg, Cr | |<--*-------|<--------*--------*--*--*--*-->| | | | | | | | | | | |
| Hospitalization | | |<---------------------------------------->| | | | | | | | | | | | |

-continued

| Total amount of blood collected 163 ml | (Prior examination) 19 ml | | 31 ml | 17 ml | 17 ml | 17 ml | 5 ml | 19 ml | | | 19 ml | (Follow-up examination) 19 ml |

3) Steps 7 and 8

| | | −24 −18 | Administration | 0 | 2 | 4 | 6 | 8 | 12 | 24 | 48 | 72 | 96 | 120 | 144 | |
|---|---|---|---|---|---|---|---|---|---|---|---|---|---|---|---|---|
| Time after administration (hr) | | | | ↓ | | | | | | | | | | | | |
| Subjective symptoms | | | | |←----------------------------------→| | | | | | | | | | | |
| Questioning, auscultation percussion | | | ○ | ○ | ○ | | ○ | | ○ | ○ | ○ | ○ | ○ | ○ | ○ | ○ |
| Vital signs | | | ○ | ○ | ○ | ○ | ○ | ○ | ○ | ○ | | | ○ | ○ | | |
| ECG | | | ○ | | | | | | ○ | ○ | | | ○ | ○ | | |
| Laboratory tests | | | ○ | | | | | | | ○ | | | ○ | ○ | | |
| Serum concentration | ST-630 Ca, P, Mg, Al—P | | ○ ○ | ○ ○ | ○ ○ | ○ ○ | ○ ○ | ○ ○ | ○ ○ | ○ ○ | ○ ○ | ○ ○ | ○ ○ | ○ ○ | | ○ |
| Urinary | ST-630 | | ○ | |←----------*---*---*---*---→| | | | | | | | | | | |
| excretion | Ca, P, Mg, Cr | |←-*-----*------*-----*--*--*--*-→| | | | | | | | | | | | | |
| Hospitalization | | | |←---------------------------------------------------------------→| | | | | | | | | | | | |

| Total amount of blood collected 284 ml | (Prior examination) 19 ml | | 31 ml | 17 ml | 17 ml | 17 ml | 17 ml | 17 ml | 17 ml | 31 ml | 17 ml | 17 ml | 17 ml | 31 ml | (Follow-up examination) 19 ml |

*: Performed only in Step 4.

2.3. Results
2.3.1. Blood biochemistry tests
No major change was found in Ca, P or Mg as shown in FIGS. 1–4.
2.3.2 Urinary excretions of electrolytes
At the 2.0 μg dose, increases in total urinary Ca excretion and urinary Ca/Cr ratio were found. Below 2.0 μg, no significant increases were found of urinary electrolytes as shown in FIGS. 5–12.
2.3.3. Summary
Eight graded doses from 0.0125 μg to 2.0 μg were used. The serum concentration of ST-630 was determined from Step. 5 (0.25 μg per dose). No change was found in blood biochemistry or in serum electrolytes. At the 2.0 μg dose, increases in total urinary Ca excretion and urinary Ca/Cr ratio were found.

3. Study of dietary effect (See FIG. 13)
3. 1. Dosing Schedule

| | Dose 2 μg | |
|---|---|---|
| Period | Number of subjects Group 1 | 5 per group Group 2 |
| I | Fasting | Postprandial* |
| II | Postprandial* | Fasting |

*: Administration at 30 min after meal.

Figure 13:
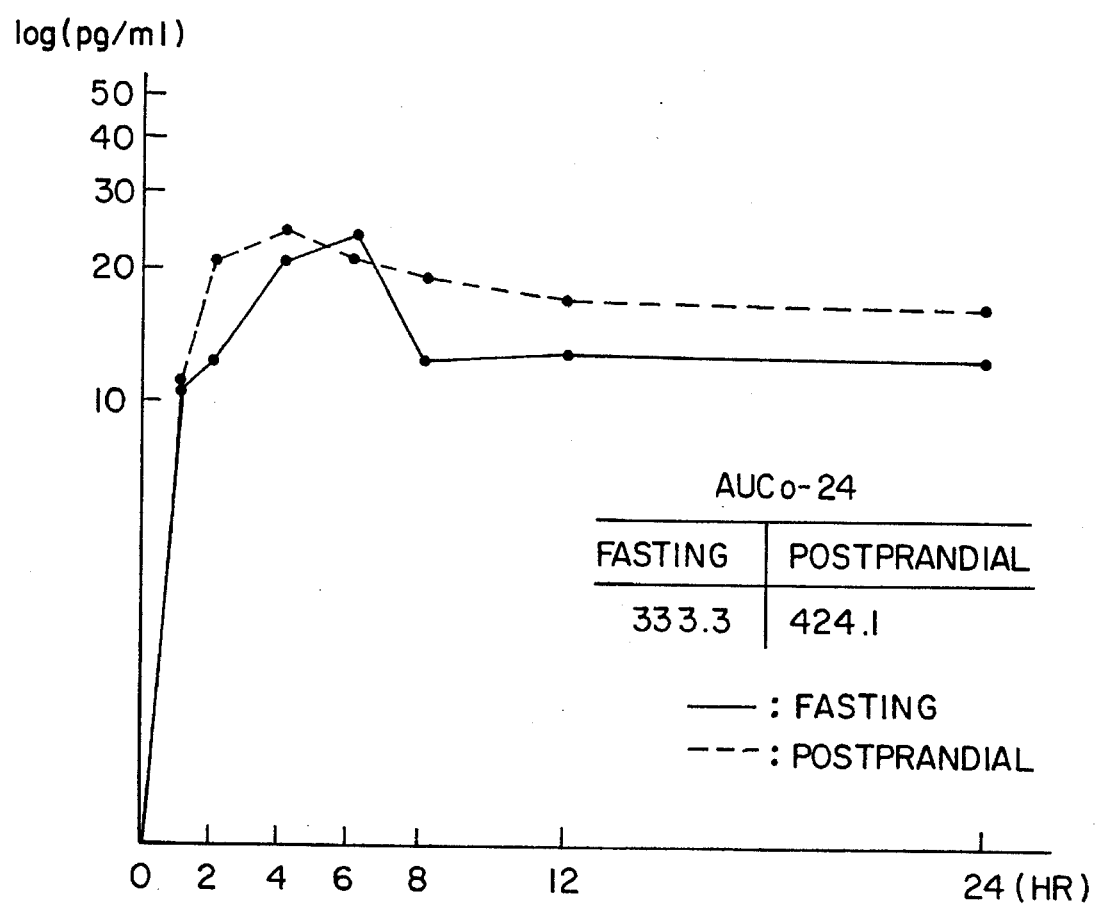
FIG. 13 is a graph illustrating the dietary effect on the absorption of ST-630 at a dose of 2.0 μg over time.
Figure 14:
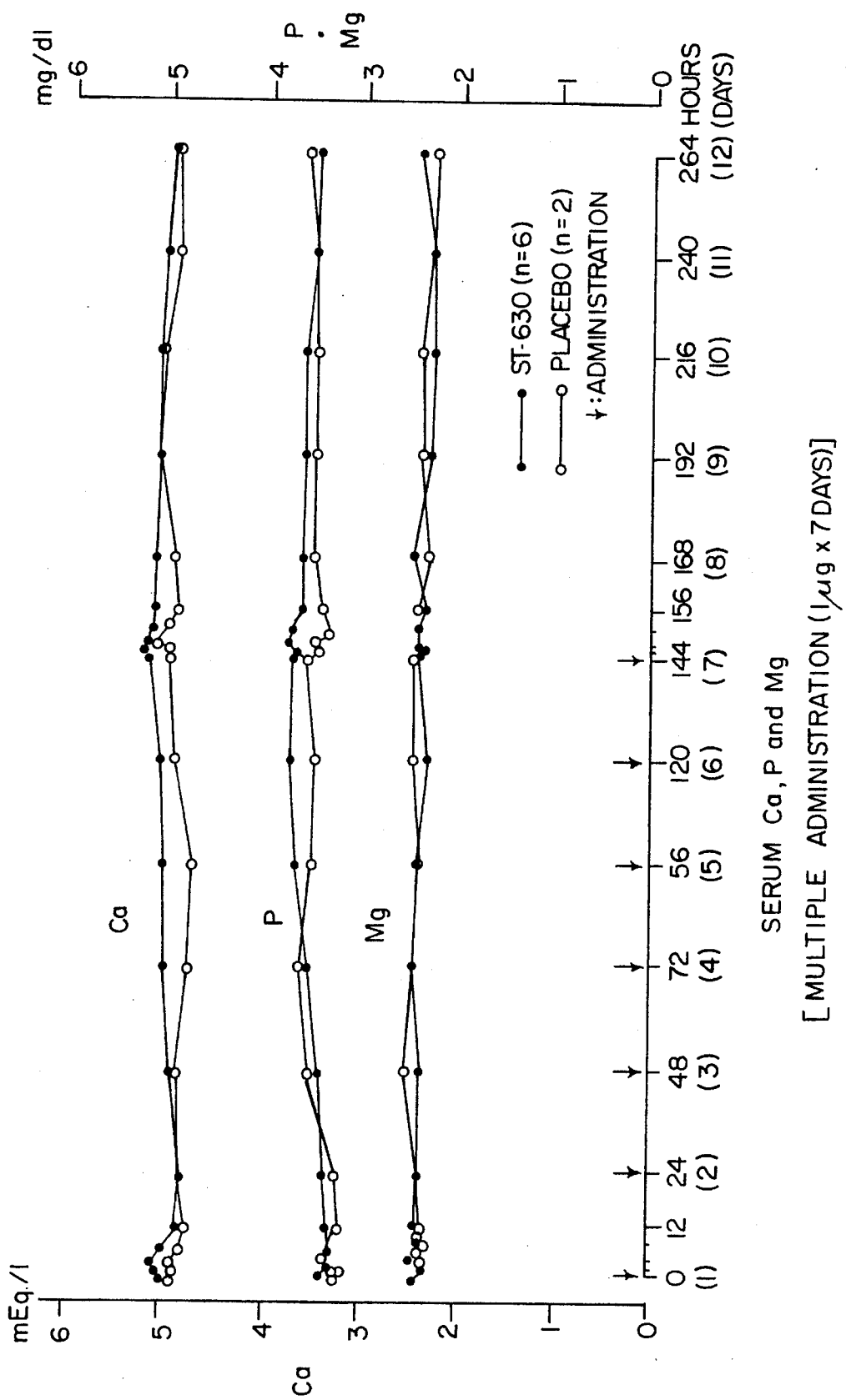
FIG. 14 is a graph of blood serum concentration of Ca, P and Mg over time after daily administration of ST-630 at a daily dose of 1.0 μg for 7 days.
Figure 15:
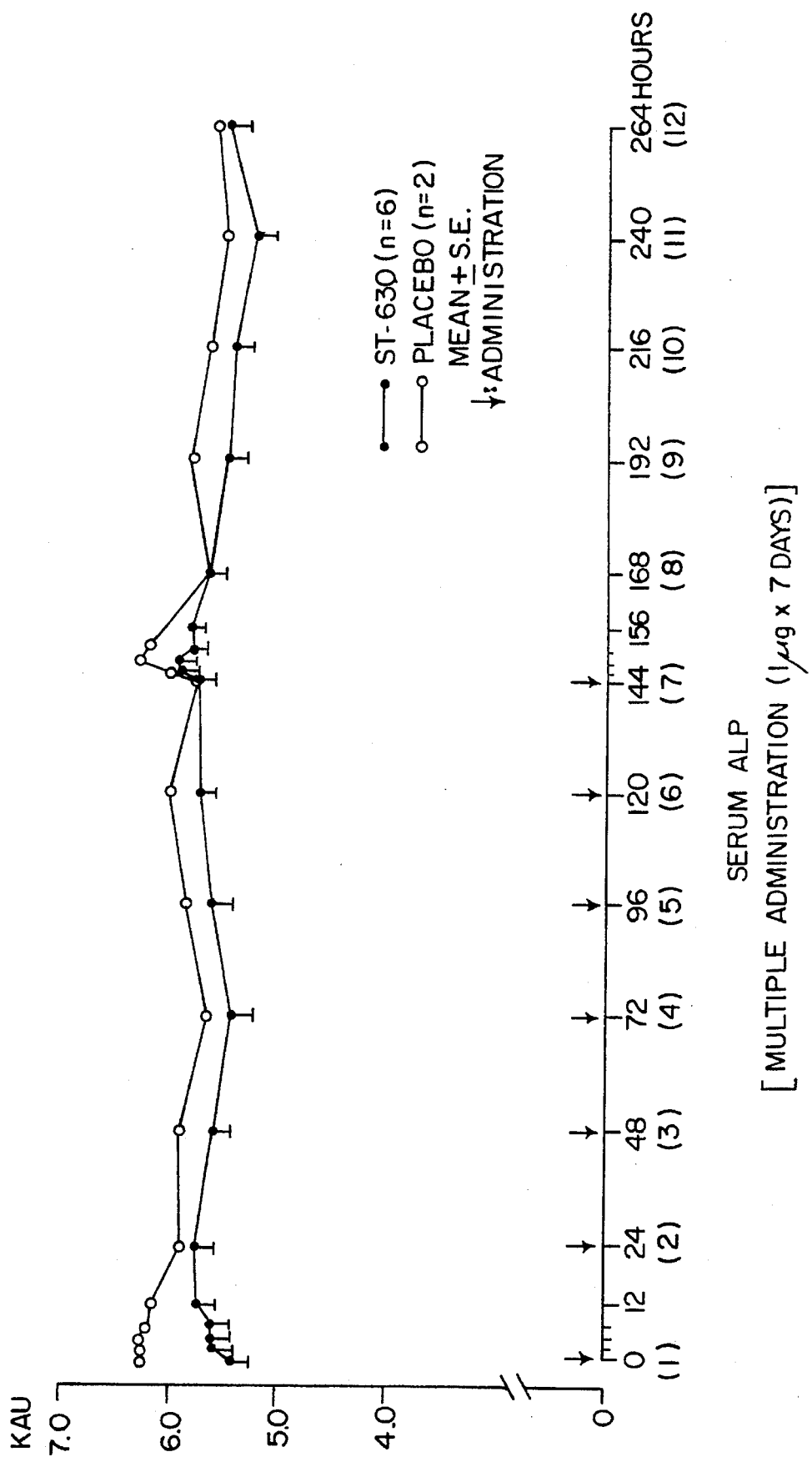
FIG. 15 is a graph of blood serum concentration of ALP over time after daily administration of ST-630 at a daily dose of 1.0 μg for 7 days.
Figure 16:
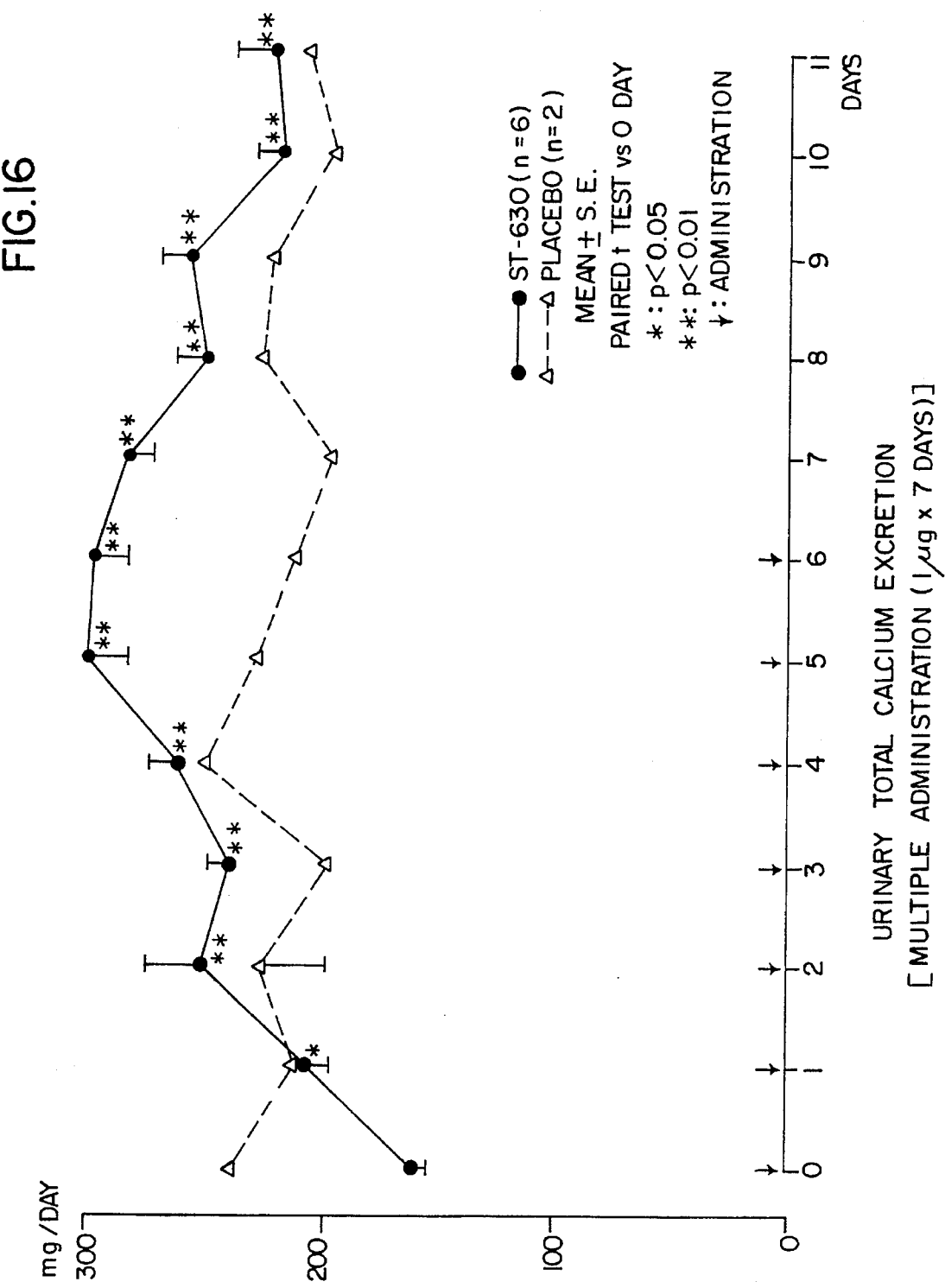
FIGS. 16–17 are graphs of urinary excretions of Ca and Ca/Cr ratio, respectively, over time after daily administration of ST-630 at a daily dose of 1 μg for 7 days.
Figure 17:
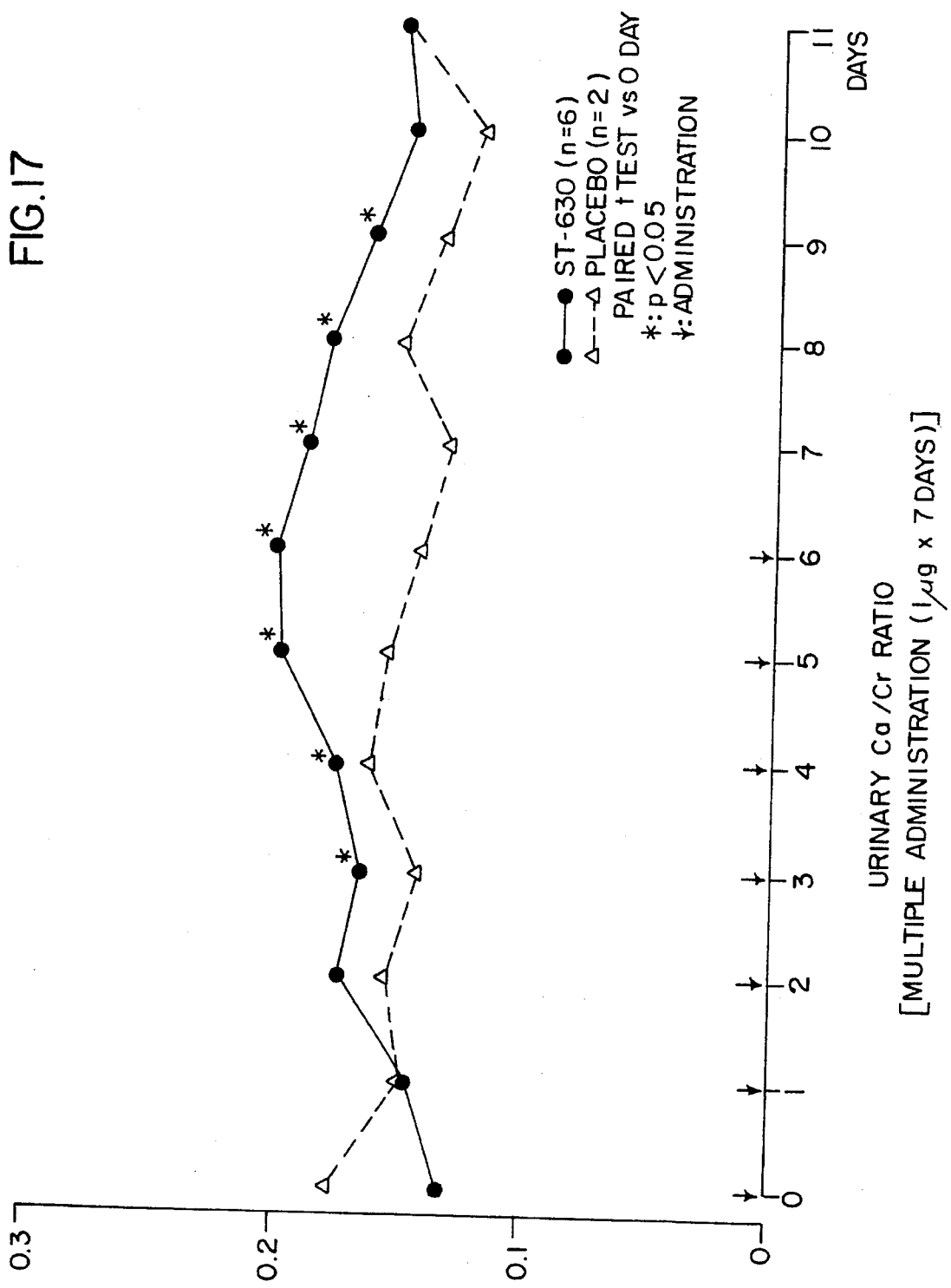
Figure 18:
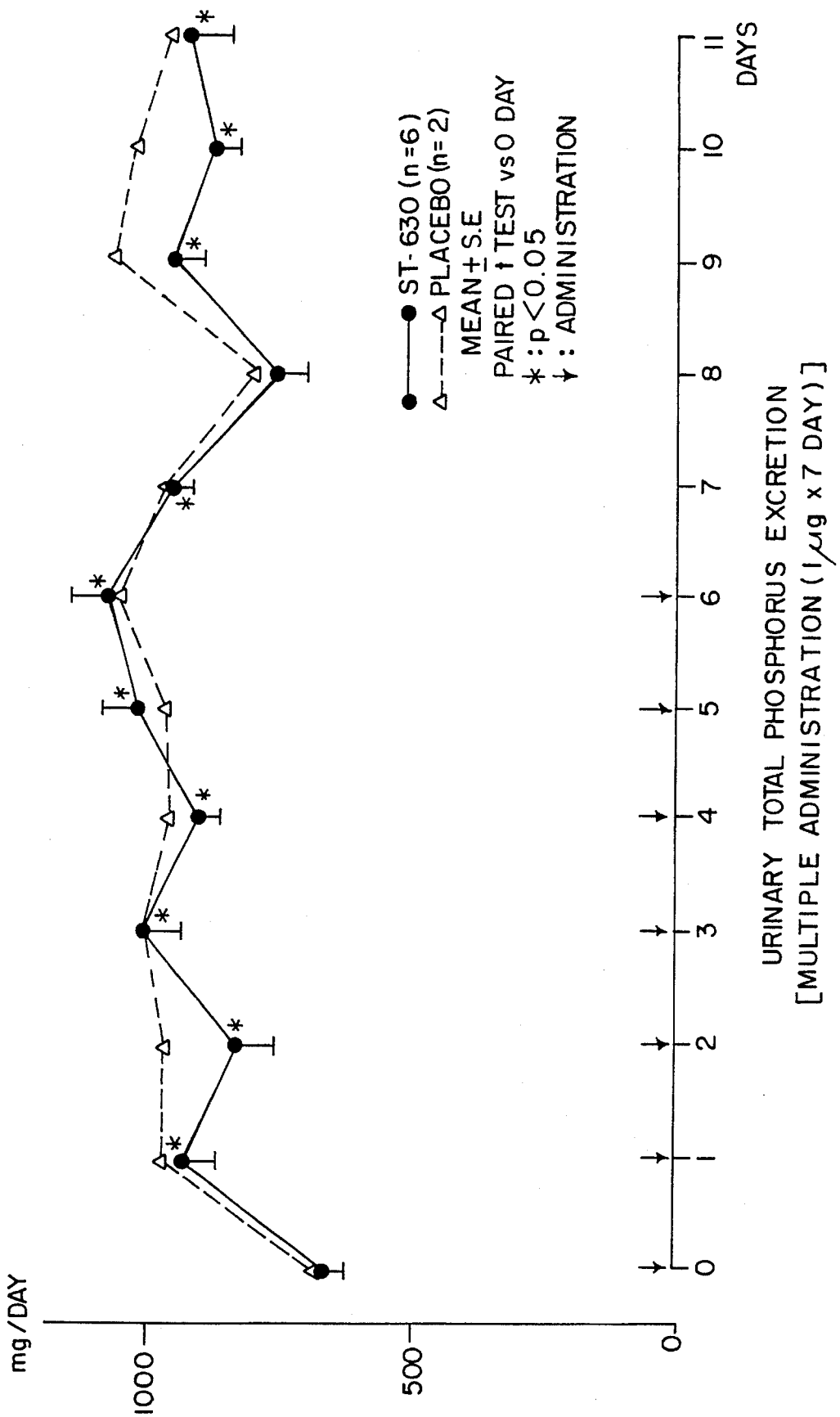
FIGS. 18–19 are graphs of urinary excretions of P and P/Cr ratio, respectively, over time after daily administration of ST-630 at a daily dose of 1 μg for 7 days.
Figure 19:
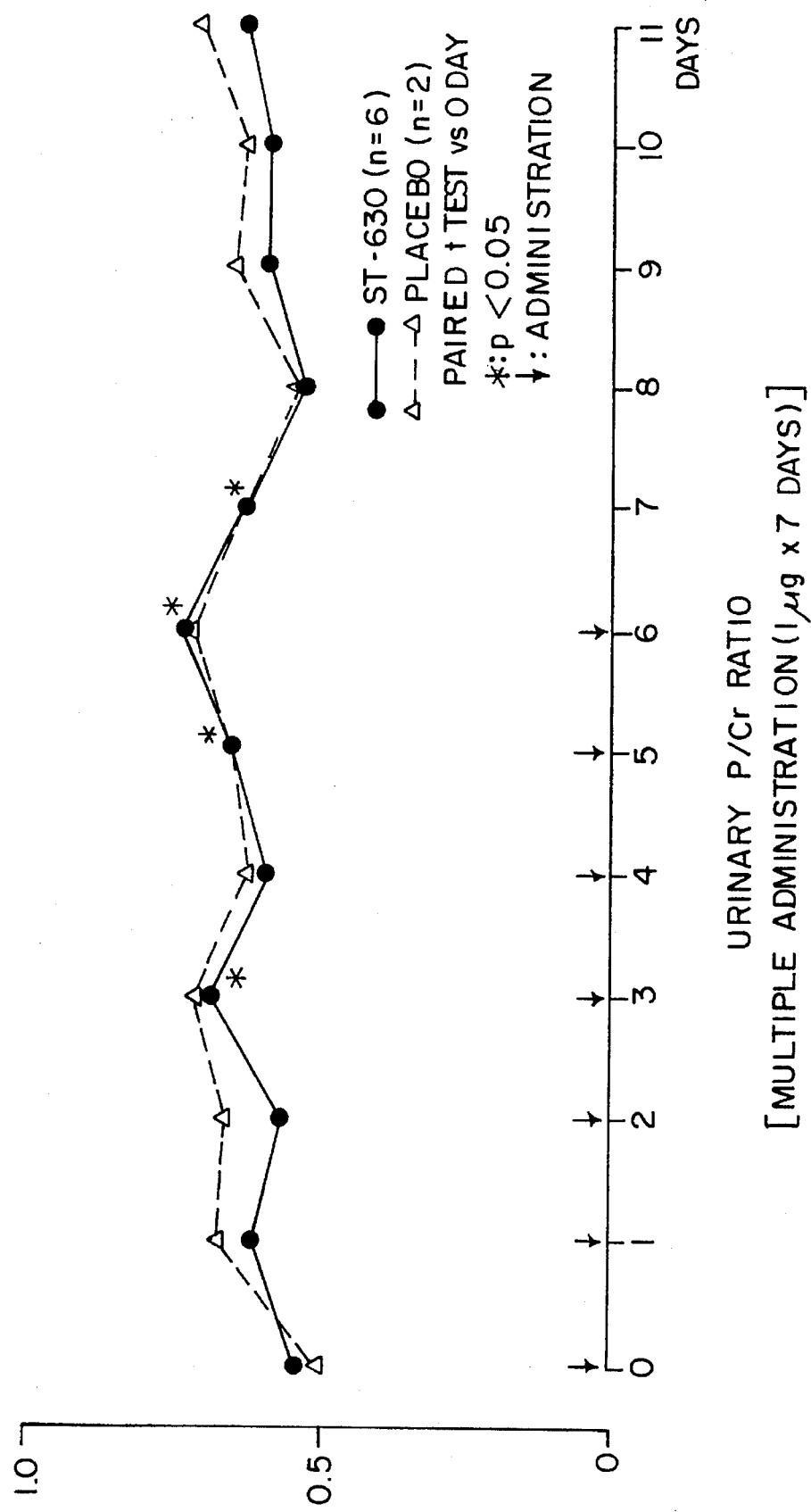
Figure 20:
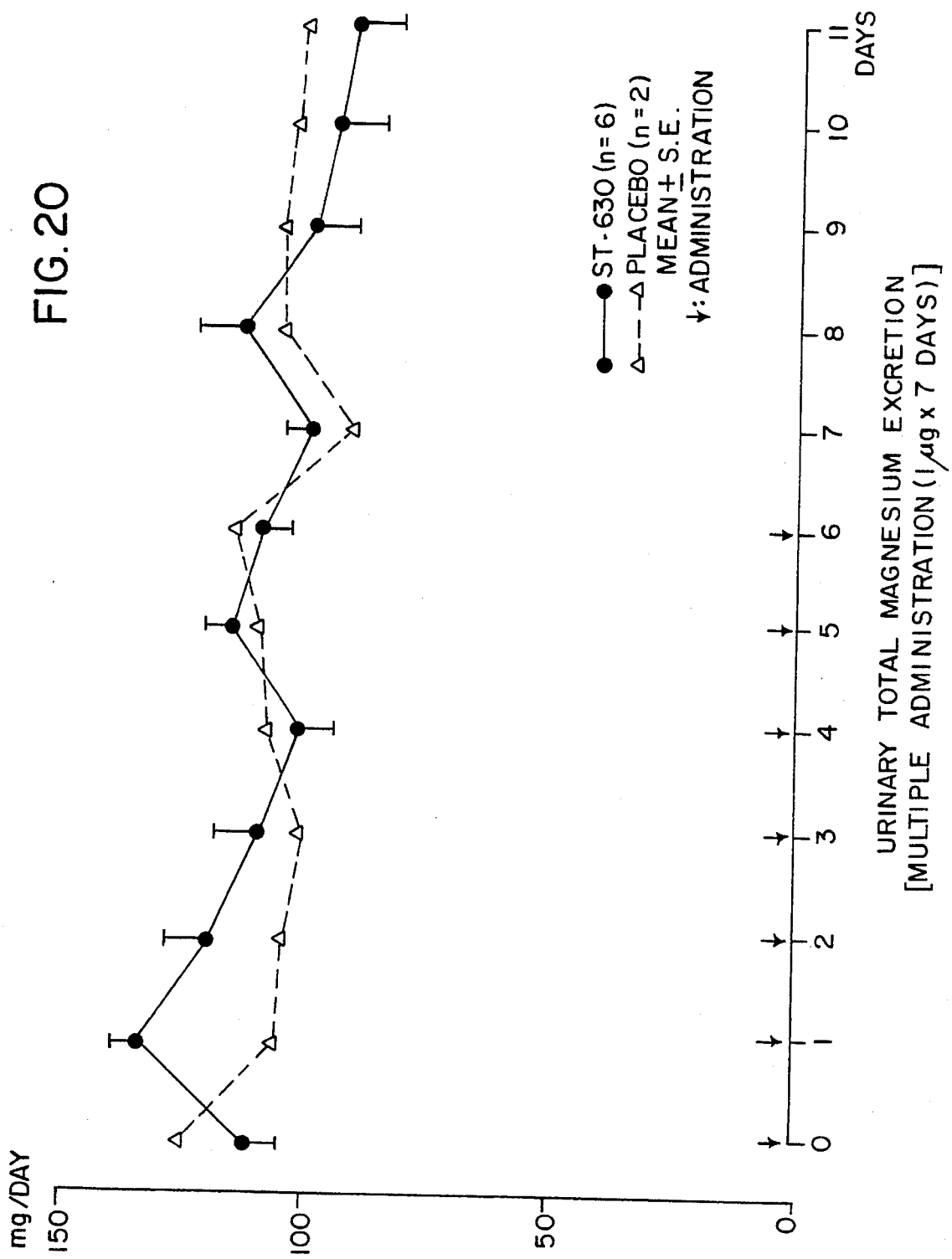
FIGS. 20–21 are graphs of urinary excretions of Mg and Mg/Cr ratio, respectively, over time after daily administration of ST-630 at a daily dose of 1 μg for 7 days.
Figure 21:
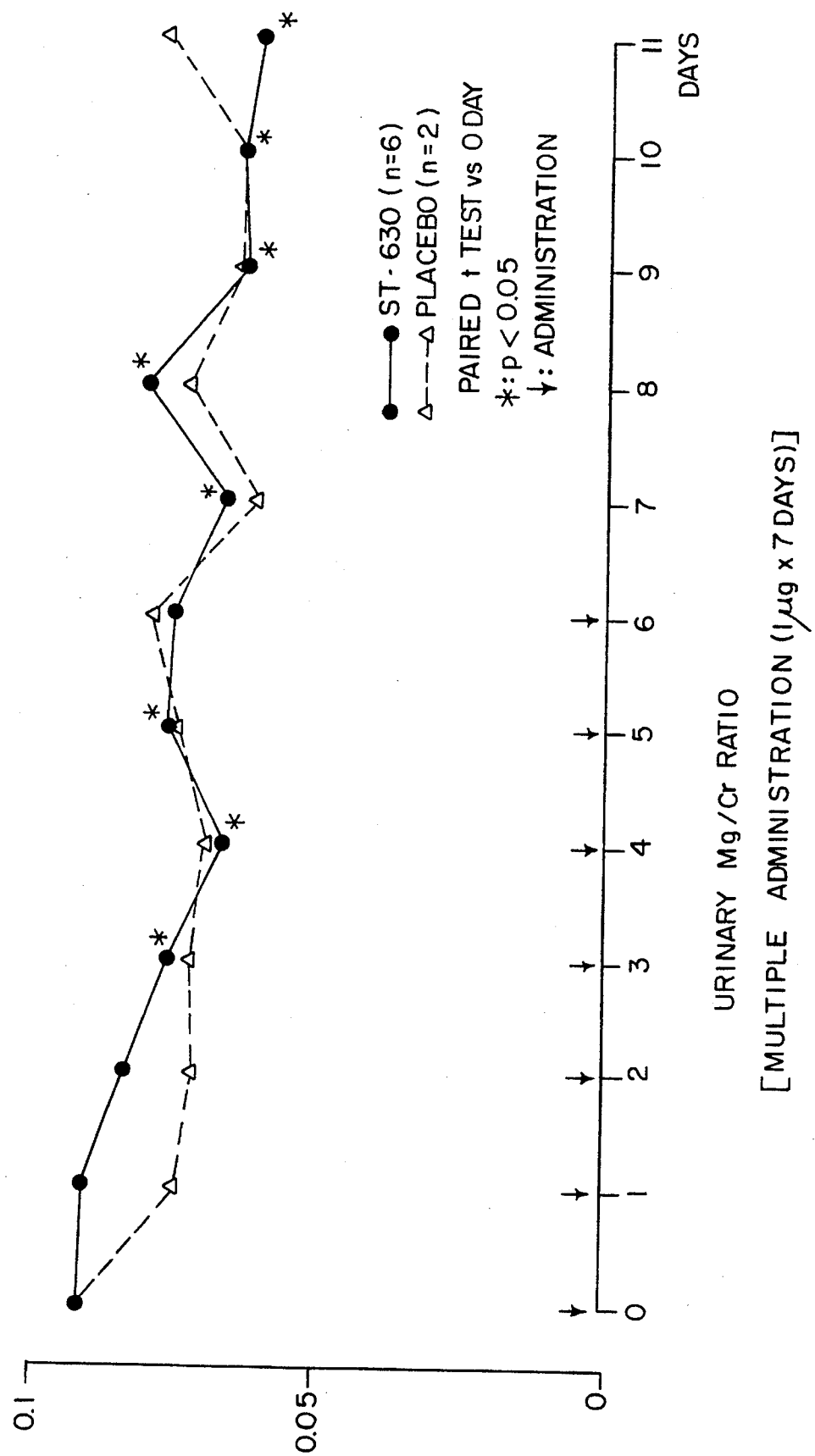
Figure 22:
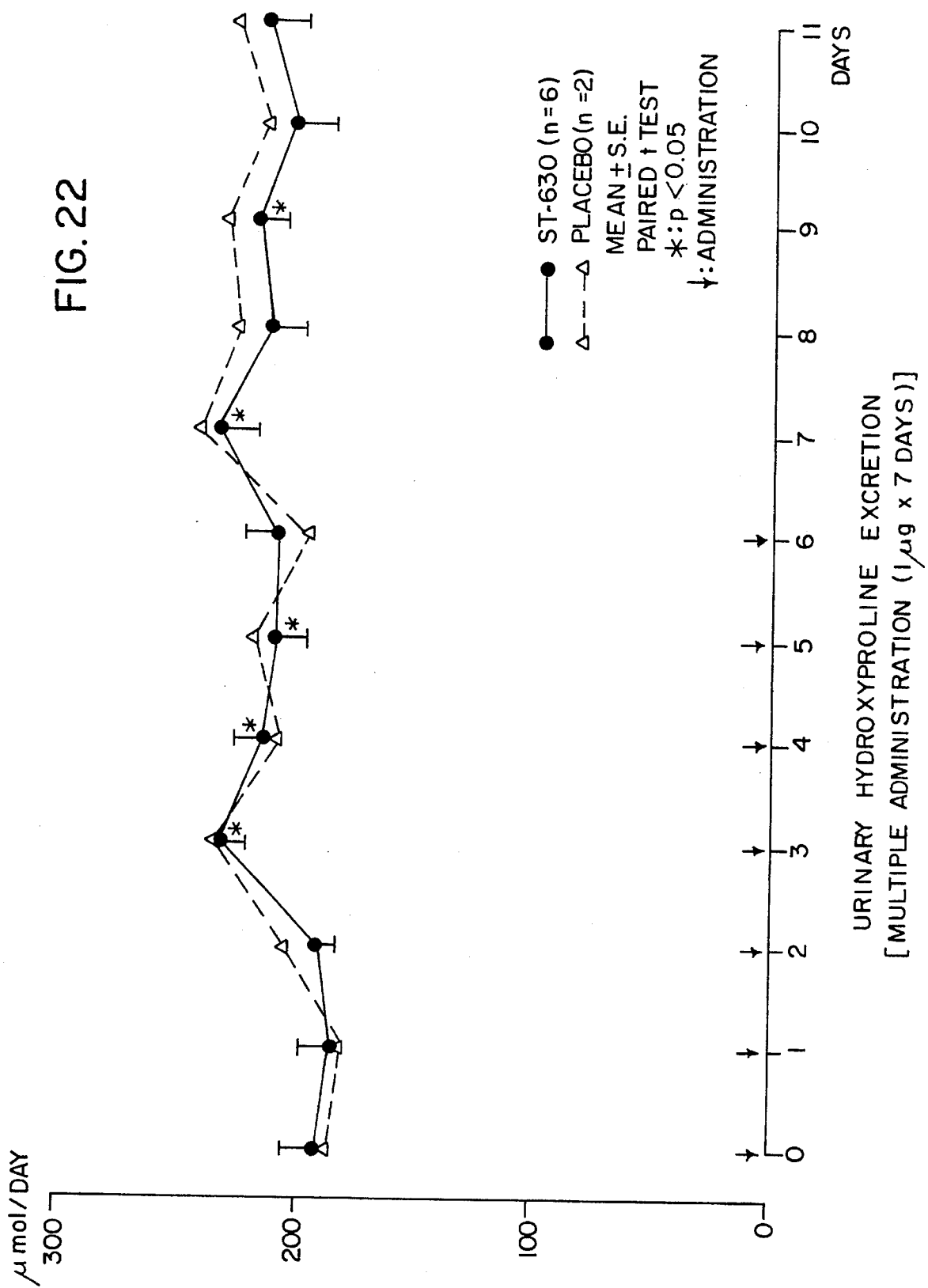
FIG. 22 is a graph of urinary excretion of hydroxyproline over time after daily administration of ST-630 at a daily dose of 1 μg for 7 days.
Figure 23:
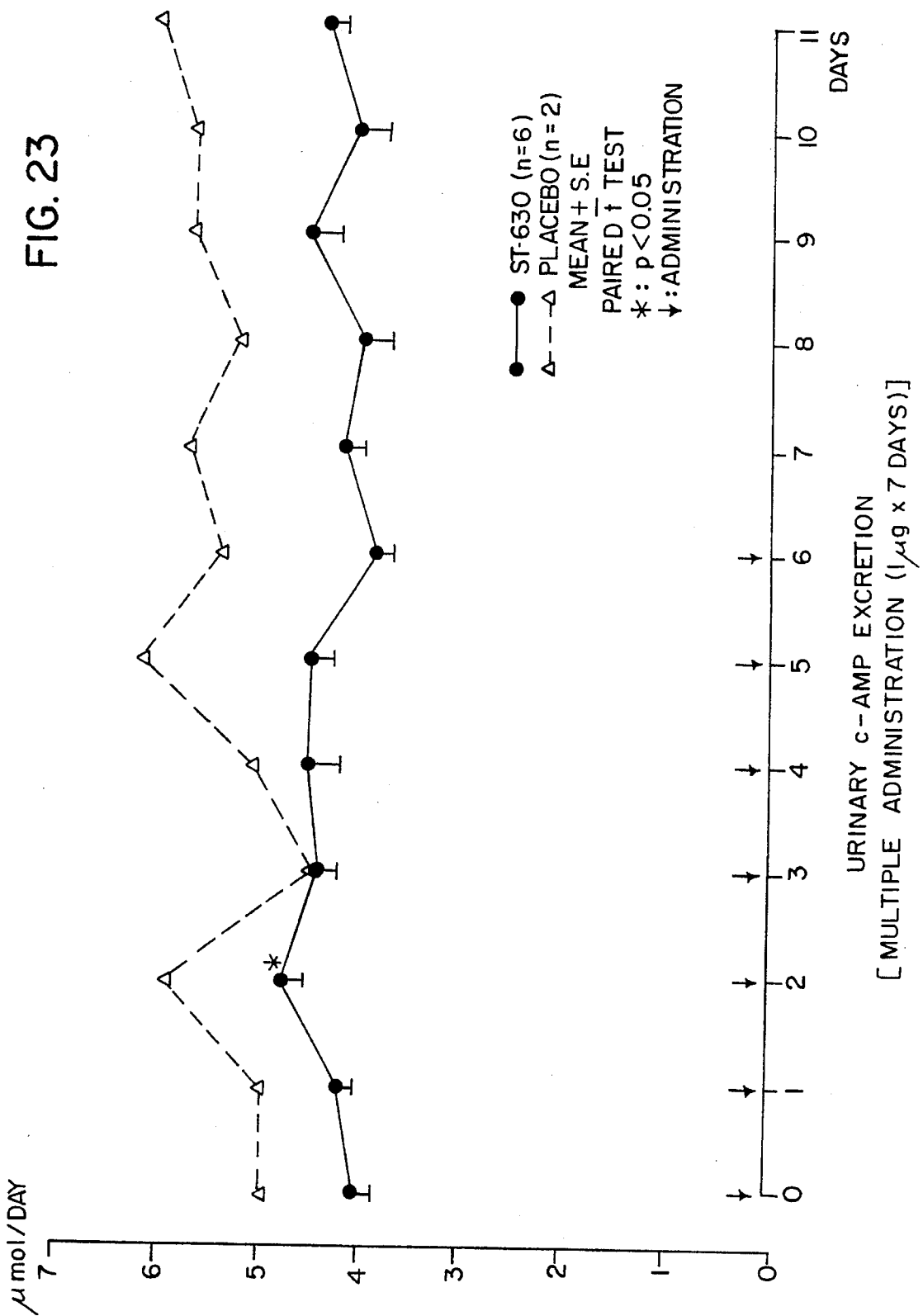
FIG. 23 is a graph of urinary cyclic AMP excretion over time after daily administration of ST-630 at a daily dose of 1 μg for 7 days.

3.2. Summary
The dietary effect on the absorption of ST-630 was studied by the crossover method at the dose of 2.0 μg. As shown in Fig. 13, the AUC (area under the serum concentration curve) of ST-630 was slightly higher after postprandial administration than administration in the fasting state.

4. Repeated-dose study (See FIGS. 14–23)
4. 1. Dosing schedule (Postprandial administration)

| Dose (μg/day) | Duration of administration (days) | Number of subjects | |
|---|---|---|---|
| | | Active drug | Placebo |
| 1.0 | 7 | 6 | 2 |

4. 2. Study schedule

| Course | Two days before treatment | The day before treatment | Administration Days 1–7 | | | | | | | Day 8 | Day 9 | Day 10 | Day 11 | Day 12 | Follow-up examination |
|---|---|---|---|---|---|---|---|---|---|---|---|---|---|---|---|
| Time after administration (hr) | | −24 | Administration | 0 | 2 | 4 | 6 | 8 | 12 | 24 | 48 | 72 | 96 | 120 | |
| Subjective symptoms | | | | |K|---|---|---|---|---|---|---|---|→| |
| Questioning, auscultation, percussion | | | ○ | | ○ | ○ | | ○ | | ○ | ○ | ○ | ○ | ○ | ○ |
| Vital signs | | | ○ | | ○ | ○ | ○ | ○ | ○ | ○ | ○ | ○ | ○ | ○ | ○ |
| ECG | | | ○ | | | | | | | ○ | ○ | | | ○ | ○ |
| Laboratory tests | | | ○*¹ | | | | | | | | ○ | | | ○ | ○ |
| Serum concentration | ST-630*² Ca, P, Mg, Al—P*³ | | ○ ○ | | ○ ○ | ○ ○ | ○ | ○ ○ | ○ ○ | ○ ○ | ○ | ○ | ○ | ○ | ○ |
| Urinary excretion | ST-630 Ca, P, Mg, Cr, K cAMP, Hy—P, Na | | ○ K---X---X---X---X---X---X---→| | | | | | | ○ | ○ | ○ | ○ | ○ | |
| Hospitalization | | | K-------------------------------------------→| | | | | | | | | | | | |
| Total amount of blood collected 354 ml | (Prior examination) 19 ml | | Day 1 of treatment: 98 ml Day 7 of treatment: 87 ml Days 2–6 of treatment: 15 ml × 5 = 75 ml | | | | | | | 15 ml | 26 ml | 3 ml | 3 ml | 14 ml | 14 ml |

*¹: Blood samples are collected only immediately before administration on day 1.
*²: Blood samples are collected only immediately before administration on days 2–6.
*³: Only cereatinie are determined immediately before and 12 hr after administration on day 1, immediately before and 12, 24, 48, 72, 96 and 120 hr after the last administration, and at follow-up examination. On days 2–6, blood samples are collected only immediately before administration.

4.3. Summary

ST-630 was administered postprandially at a daily dose of 1.0 μg for 7 days. The serum Ca concentration tended to be elevated slightly but the change was within the normal range. The urinary Ca/Cr ratio increased with the number of dosings but recovered to the control value immediately after completion of administration.

5. Subjective and objective symptoms

| Study step | Dose (μg/day) | Date of initiation of treatment | Subject No. | Symptom | Time of onset and duration | Drug |
|---|---|---|---|---|---|---|
| | | | Single-dose administration | | | |
| 1 | 0.0125 | Feb. 2, 1988 | 1 | ESR | Follow-up examination (2/15) Date: before 2/4 2/8 2/15 3/26  1 h    3    3    3    13  1  2 h          7    8    8    34  8 | Active drug |
| | | | 2 | Mild headache | for 4.5 hr from 6 hr after administration | Placebo |
| 5 | 0.25 | May 19, 1988 | 8 | Headache | After administration till bedtime | Active Drug |
| 8 | 2.0 | Aug. 13, 1988 | 6 | Mild headache Mild feverish sensation | for 3.5 hr from 3 hr after administration Course of body temparature Before 35.5°, 2 h 35.5°, 4 h 35.9°, 6 hr 36.6°, 8 hr 36.6°, 12 hr 37.0°, 24 h 35.6°, 48 h 35.3° | Placebo |
| | | | 8 | ESR | Follow-up examination (8/27) Date: before 8/15 8/19 8/27 9/6  1 h    5    4    4    11  3  2 h          8    4    11    27  8 | Active Drug |

| | | -continued | |
|---|---|---|---|
| | | Dietary effect | |
| 2.0 | Nov. 17, 1988 | 1–10 | None |
| 2.0 | Dec. 1, 1988 | 1–10 | None |
| | | Repeated-dose adimnistration | |
| 1.0, 7 days | Feb. 17, 1989 | 1–8 | None |

5.1. Summary

With regard to subjective and objective symptoms, headache was found in one case in Step 5 (0.25 µg) and an increase in erthrocyte sedimentation rate was observed in one case each in Step 1 (0.0125 µg) and Step 8 (2.0 µg) in the single-dose study. No symptom was found in the study of dietary effect or in the repeated-dose study.

Thus, ST-630 promoted calcium absorption but caused no hypercalcemia, indicating no remarkable problem on safety. The "window" or tolerance between effectiveness and toxicity of ST-630 in humans is thus relatively large.

It can be concluded from the foregoing data that $26,26,26,27,27,27$-$F_6$-$1\alpha,25$-$(OH)_2D_3$ may be administered to patients having a variety of human diseases resulting from calcium metabolism disorders on a long term basis. For example, diseases such as renal osteodystrophy, hypoparathyroidism, pseudohypoparathyroidism, hypocalcemia, osteomalacia, vitamin D-deficient rickets and various forms of osteoporosis such as postmenopausal osteoporosis, estrogen-lack osteoporosis, senile osteoporosis and steroid-induced osteoporosis may be treated with ST-630. In particular, the foregoing data shows that $26,26,26,27,27,27$-$F_6$-$1\alpha,25$-$(OH)_2D_3$ may be administered in the manner and dosages described below.

The $26,26,26,27,27,27$-$F_6$-$1,25$-$(OH)_2D_3$ used in the method of this invention may be readily administered in sterile parenteral solutions by injection or intravenously or by alimentary canal in the form of oral dosages, or transdermally, or by suppository. Doses of from about 0.05 µg to about 2.0 µg per day of 26,26,26,27,27,27-hexafluoro 1α,25-dihydroxyvitamin $D_3$ compound per se, or in combination with other 1α-hydroxylated vitamin D compounds, are effective in obtaining physiological responses which are characteristic of vitamin D-like activity, with maintenance doses of about 0.1 µg to 1.0 µg being suitable for at least the above-described time period without inducing patient toxicity.

The proportions of the hexafluoro compound, or of each of the compounds in the combination, are dependent upon the particular disease state being addressed and the degree of response desired. Amounts in excess of about 2.0 micrograms per day of the hexafluoro compound or the combination of that compound with other 1α-hydroxylated vitamin D compounds, are generally unnecessary to achieve the desired results, may result in hypercalcemia, and may not be an economically sound practice. In practice the higher doses are used where therapeutic treatment of a disease state is the desired end while the lower doses are generally used for prophylactic purposes, it being understood that the specific dosage, administered in any given case will be adjusted in accordance with the specific compounds being administered, the disease to be treated, the condition of the subject and the other relevant medical facts that may modify the activity of the drug or the response of the subject, as is well known by those skilled in the art. In general, either a single daily dose or divided daily dosages may be employed, as is well known in the art.

Dosage forms of the compound can be prepared by combining them with a non-toxic pharmaceutically acceptable carrier to make either immediate or slow release formulations as is well known in the art. Such carriers may be either solid or liquid such as, for example, corn starch, lactose, sucrose, peanut oil, olive oil, sesame oil, propylene glycol and water. If a solid carrier is used the dosage forms of the compounds of the invention may be tablets, capsules, powders, troches or lozenges. If a liquid carrier is used, soft gelatin capsules, or syrup or liquid suspensions, emulsions or solutions may be the dosage form. The dosage forms may also contain adjuvants, such as preserving, stabilizing, wetting or emulsifying agents, solution promoters, etc. They may also contain other therapeutically valuable substances.

It should be understood that although dosage ranges are given the particular dose to be administered to a host will depend upon the specific disease state being treated and the end results being sought in a particular case, as well as other factors known to those skilled in the art in the therapeutic use of such medicinal agents.

Ovariectomized Rate Model

Female Fisher rats, 9–10 months old, were ovariectomized and were fed a vitamin D-deficient diet containing 0.45% calcium and 0.3% phosphorus. The rats were given 15IU of vitamin $D_3$ orally once a week throughout this experiment. Four weeks after the surgery, the rats were orally adminstered three times a week for 23 weeks with ST-630 (30, 100 or 300 pmole/kg) or 1α-hydroxyvitamin $D_3$ (100 or 300 pmole/kg).

The data show both serum calcium and phosphorus levels were increased dose-dependently with the treatment of ST-630 or 1α-hydroxyvitamin $D_3$ (Table 1). Also, ST-630 prevented the decrease of dry weight, ash weight and breaking load of the femur more potently than 1α-hydroxyvitamin $D_3$ (Table 1).

Figure 24:
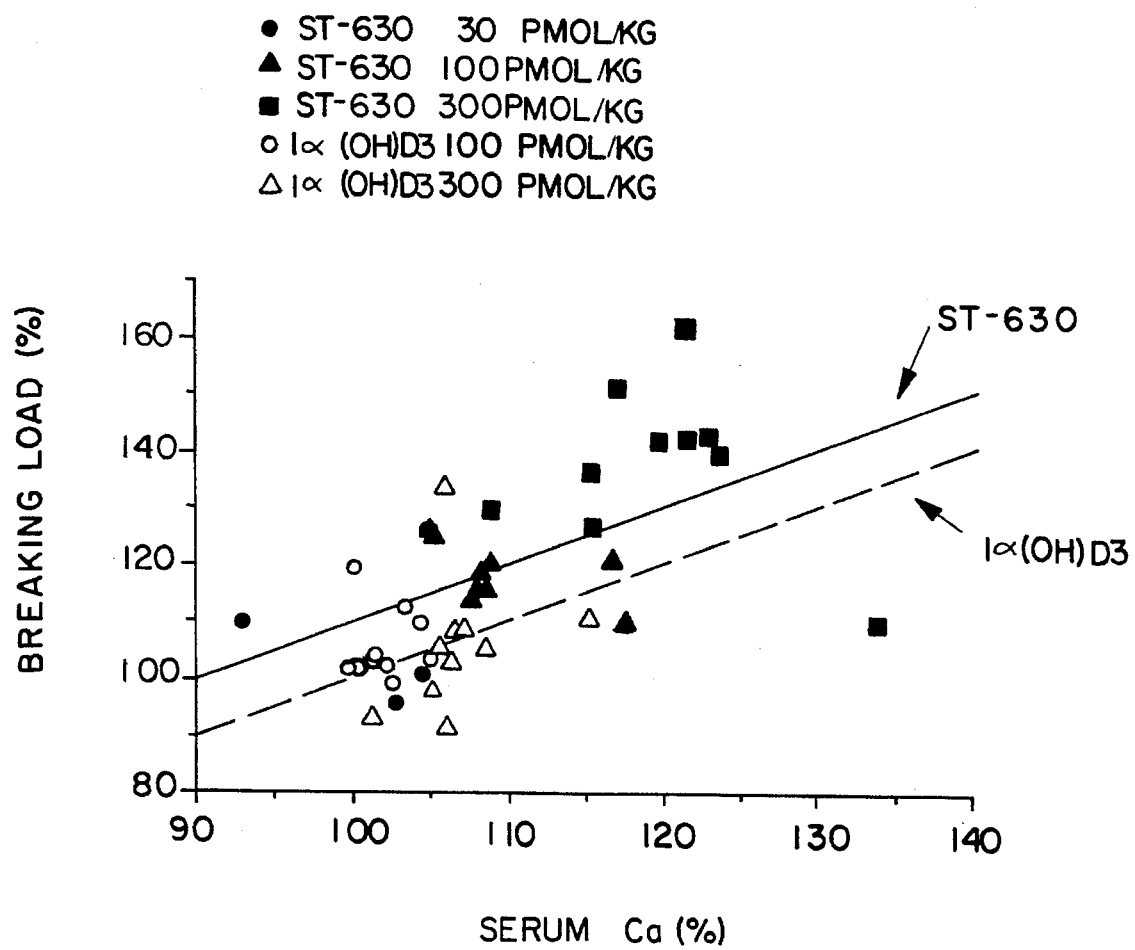
FIG. 24 is a graph of the relationship between serum calcium and breaking load of the femur in ovariectomized rats treated with ST-630 and 1α-hydroxyvitamin $D_3$ at various doses.

The correlation between the increase of the breaking load of the femur and the increase of serum calcium levels showed that ST-630 increased the mechanical strength of the bone more potently than 1α-hydroxyvitamin $D_3$ at the doses in which each drug cause the increase of serum calcium levels to the same content (FIG. 24).

Toxicity $LD_{50}$ data represent the dose administered resulting in the death of 50% of the test group. For a single (acute) dose in male rats, the $LD_{50}$ at 14 days for ST-630 was 0.043 mg/kg and for 1α-hydroxyvitamin $D_3$ was 0.2 mg/kg. It thus appears that ST-630 is about five times more toxic than 1α-hydroxyvitamin $D_3$ in rats.

With respect to chronic dosing, a group of six female beagle dogs were given 0.3 mg/kg of either ST-630 or 1α-hydroxyvitamin $D_3$ orally each day for three months. At the end of three months, all six dogs being administered ST-630 had died whereas only two of six dogs being administered 1 α-hydroxyvitamin $D_3$ died. These data support the conclusion that, in rats and dogs, ST-630 is much more toxic than 1α-hydroxyvitamin $D_3$.

Typically, 1 μg/day is the safe dose used for human administration of 1α-hydroxyvitamin $D_3$. The above toxicity data in rats and dogs would thus lead one to believe that 0.2 μg/day of ST-630 would be an appropriate upper limit dosage for administration in humans since the above $LD_{50}$ data show ST-630 is five times more toxic than 1α-hydroxyvitamin $D_3$. Instead, ST-630 can be administered in much higher doses to humans without toxicity problems as shown by the data in FIG. 2 (0.5 μg), FIG. 3 (1 μg) and FIG. 4 (2 μg). Thus, the ability to administer higher doses of ST-630 without resultant toxicity problems means ST-630 will be more effective against osteoporosis.

TABLE 1

Effects of ST-630 and 1α(OH)$D_3$ on Serum Calcium and Phosphorus and the Femur in Ovariectomized Rats

| Group Dose (pmole/kg p.o.) | Sham | OVX | ST-630 | | | 1α(OH)$D_3$ | |
|---|---|---|---|---|---|---|---|
| | | | 30 | 100 | 300 | 100 | 300 |
| Serum Ca (mg/100 ml) | 9.9 ± 0.4 | 9.7 ± 0.2 | 9.9 ± 0.4 | 10.6 ± 04** | 11.7 ± 0.7** | 9.9 ± 0.2 | 10.3 ± 0.3 |
| Serum Pi (mg/100 ml) | 2.7 ± 0.5 | 2.6 ± 0.4 | 3.6 ± 0.3** | 4.8 ± 0.2** | 5.3 ± 0.3** | 3.8 ± 0.3** | 4.3 ± 0.4** |
| Dry weight (mg) | 455 ± 26 | 431 ± 26 | 449 ± 29 | 472 ± 21* | 538 ± 47** | 454 ± 42 | 461 ± 47 |
| Ash weight (mg) | 300 ± 19 | 285 ± 19 | 298 ± 22 | 319 ± 12* | 362 ± 32** | 303 ± 29 | 308 ± 33 |
| Breaking load (kg) | 9.7 ± 0.8 | 9.0 ± 0.9 | 9.7 ± 0.8 | 10.6 ± 0.5** | 12.4 ± 1.3** | 9.3 ± 0.6 | 9.5 ± 1.1 |

Mean ± SD (N = 8 ~ 10)
*p < 0.05,
**pp < 0.01 significantly different from OVX

We claim:

1. A method of treating postmenopausal osteoporosis in humans which comprises administering to a subject having said postmenopausal osteoporosis an effective daily dose of 26,26,26,27,27,27-hexafluoro-1α,25-dihydroxy-cholecalciferol compound in an amount of from about 0.05 μg to about 2.0 μg.

2. The method of claim 1, wherein said compound is combined with a non-toxic pharmaceutically acceptable carrier and is administered in liquid form.

3. The method of claim 2 Wherein said compound is administered by injection.

4. The method of claim 2 wherein said compound is administered intravenously.

5. The method of claim 2 wherein said compound is administered orally.

6. The method of claim 1 wherein said compound is combined with a non-toxic pharmaceutically acceptable carrier and is administered in solid form.

7. The method of claim 6 wherein said compound is adminstered by suppository.

8. The compound of claim 6 wherein said compound is administered orally.

9. A method of treating postmenopausal osteoporosis in humans which comprises administering to a subject having said postmenopausal osteoporosis an effective treatment dosage of 26,26,26,27,27,27-hexafluoro-1α,25-dihydroxycholecalciferol compound in an amount from about 0.05 μg to about 2.0 μg per day, and thereafter administering an effective maintenance dosage of said compound in an amount from about 0.1 μg to about 1.0 μg per day.

10. The method of claim 9 wherein said compound is combined with a non-toxic pharmaceutically acceptable carrier and is administered in liquid form.

11. The method of claim 10 wherein said compound is administered by injection.

12. The method of claim 10 wherein said compound is administered intravenously.

13. The method of claim 10 wherein said compound is administered orally.

14. The method of claim 9 wherein said compound is combined with a non-toxic pharmaceutically acceptable carrier and is administered in solid form.

15. The method of claim 14 wherein said compound is administered by suppository.

16. The method of claim 14 wherein said compound is administered orally.

17. The method of claim 9 wherein said effective treatment dosage is administered daily for a minimum of 7 days.

18. A method of treating postmenopausal osteoporosis which comprises administering to a subject having postmenopausal osteoporosis an effective daily dose of 26,26,26,27,27,27-hexafluoro-1α,25-dihydroxy-cholecalciferol compound in an amount of from about 0.05 μg to about 2.0 μg for a minimum of 7 days.

19. The method of claim 18 further including the step of thereafter administering an effective maintenance dosage of said compound in an amount from about 0.1 μg to about 1.0 μg per day for a minimum of 7 days.

* * * * *

UNITED STATES PATENT AND TRADEMARK OFFICE
CERTIFICATE OF CORRECTION

PATENT NO. : 5,571,802
DATED : November 5, 1996
INVENTOR(S) : Hector F. DeLuca et al It is certified that error appears in the above-indentified patent and that said Letters Patent is hereby corrected as shown below:

Column 1, after the title, insert the following:

---This invention was made with United States Government support awarded by the National Institutes of Health (NIH), Grant #DK-14881. The United States Government has certain rights in this invention.---

Signed and Sealed this

First Day of April, 1997

BRUCE LEHMAN

*Attest:*

*Attesting Officer*  *Commissioner of Patents and Trademarks*